US011478343B2

(12) United States Patent
Min

(10) Patent No.: US 11,478,343 B2
(45) Date of Patent: Oct. 25, 2022

(54) APPARATUS CONFIGURED TO BE ATTACHABLE AND DETACHABLE TO AND FROM ORAL CAVITY

(71) Applicant: Seungki Min, Yongin-si (KR)

(72) Inventor: Seungki Min, Yongin-si (KR)

( * ) Notice: Subject to any disclaimer, the term of this patent is extended or adjusted under 35 U.S.C. 154(b) by 182 days.

(21) Appl. No.: 16/770,340

(22) PCT Filed: Nov. 29, 2018

(86) PCT No.: PCT/KR2018/014961
§ 371 (c)(1),
(2) Date: Jun. 5, 2020

(87) PCT Pub. No.: WO2019/112244
PCT Pub. Date: Jun. 13, 2019

(65) Prior Publication Data
US 2020/0375712 A1 Dec. 3, 2020

(30) Foreign Application Priority Data
Dec. 6, 2017 (KR) .................. 10-2017-0166931

(51) Int. Cl.
*A61C 19/04* (2006.01)
*A61C 7/00* (2006.01)
(Continued)

(52) U.S. Cl.
CPC .............. *A61C 19/04* (2013.01); *A61C 7/002* (2013.01); *A61C 7/08* (2013.01); *G16H 40/63* (2018.01)

(58) Field of Classification Search
CPC ........... A61C 19/04; A61C 7/002; A61C 7/08; A61C 7/00; G16H 40/63; A61B 5/685;
(Continued)

(56) References Cited

U.S. PATENT DOCUMENTS 4,299,568 A * 11/1981 Crowley .................. A61C 7/00
 433/6
11,219,506 B2 * 1/2022 Shanjani ................ A61C 19/05
(Continued)

FOREIGN PATENT DOCUMENTS

EP 3376159 A1 * 9/2018 ........... A61B 5/4205
EP 3409183 A1 * 12/2018 ........... A61B 5/0062
(Continued)

OTHER PUBLICATIONS

International Search Report dated May 28, 2019 in corresponding International Application No. PCT/KR2018/014961; 5 pages.

*Primary Examiner* — Jacqueline T Johanas
*Assistant Examiner* — Holly T. To
(74) *Attorney, Agent, or Firm* — Maier & Maier, PLLC

(57) ABSTRACT

A device includes an antenna, markers disposed inside the device and configured to be movable inside the device to measure positions of a first tooth and a second tooth among teeth in the oral cavity, a sensor module measuring positions of the markers, and at least one of a distance between a reference point set in the device and at least one of the first tooth and the second tooth and a distance between the first tooth and the second tooth based on the measured positions of the plurality of markers. The device further includes a communication module transmitting to an external device at least one of information about the measured distance between the reference point set in the device and the at least one of the first tooth and the second tooth and information about the measured distance between the first tooth and the second tooth through the antenna.

9 Claims, 13 Drawing Sheets

(51) Int. Cl.
*A61C 7/08* (2006.01)
*G16H 40/63* (2018.01)

(58) Field of Classification Search
CPC ... A61B 5/1111; A61B 5/0002; A61B 5/6802; A61B 5/682; A61B 5/150954; A61B 5/6843
USPC .......................................................... 433/72
See application file for complete search history.

(56) References Cited

U.S. PATENT DOCUMENTS

| | | | | |
|---|---|---|---|---|
| 2003/0078528 | A1* | 4/2003 | Rahman | A61B 5/4833 602/5 |
| 2005/0118555 | A1* | 6/2005 | Sporbert | A61C 19/04 433/213 |
| 2006/0127836 | A1* | 6/2006 | Wen | A61C 19/04 433/24 |
| 2006/0223022 | A1* | 10/2006 | Solomon | A61C 7/08 433/6 |
| 2009/0210032 | A1* | 8/2009 | Beiski | A61N 1/0548 607/59 |
| 2014/0081091 | A1* | 3/2014 | Abolfathi | A61B 5/0022 600/301 |
| 2014/0248574 | A1* | 9/2014 | Yoon | A61C 13/08 433/199.1 |
| 2014/0295372 | A1* | 10/2014 | Haenggi | A61C 19/04 433/72 |
| 2014/0350354 | A1* | 11/2014 | Stenzler | A61F 5/566 600/301 |
| 2015/0289806 | A1* | 10/2015 | Hoke | A61C 19/045 433/180 |
| 2015/0305669 | A1* | 10/2015 | Hultgren | G16H 40/67 433/27 |
| 2015/0343208 | A1* | 12/2015 | Davidovitch | A61N 1/0548 433/6 |
| 2016/0267771 | A1* | 9/2016 | Baek | H04B 1/385 |
| 2016/0367188 | A1* | 12/2016 | Malik | G16H 40/67 |
| 2017/0173262 | A1* | 6/2017 | Veltz | G16H 20/17 |
| 2017/0251954 | A1* | 9/2017 | Lotan | A61B 5/1076 |
| 2017/0252140 | A1* | 9/2017 | Murphy | A61C 7/10 |
| 2017/0340411 | A1* | 11/2017 | Akselrod | A61C 8/0093 |
| 2018/0000563 | A1* | 1/2018 | Shanjani | H04B 5/0056 |
| 2018/0014747 | A1* | 1/2018 | Akselrod | A61B 5/0531 |
| 2018/0085059 | A1* | 3/2018 | Lee | A61B 5/07 |
| 2018/0368961 | A1* | 12/2018 | Shanjani | A61K 49/0004 |
| 2019/0231477 | A1* | 8/2019 | Shanjani | A61C 19/045 |
| 2019/0358008 | A1* | 11/2019 | Toimela | A61B 6/4085 |
| 2021/0038153 | A1* | 2/2021 | Claflin | A61B 5/0004 |
| 2021/0186668 | A1* | 6/2021 | Falkel | A61C 9/0046 |

FOREIGN PATENT DOCUMENTS

| | | | | |
|---|---|---|---|---|
| EP | 3598935 A1 | * | 1/2020 | ............ A61B 5/682 |
| JP | 2020141789 A | * | 9/2020 | ............ A61C 7/08 |
| KR | 20150022018 A | * | 3/2015 | ............ A61B 6/032 |
| KR | 20160040076 A | * | 4/2016 | ............ H04M 19/04 |
| KR | 10-2016-0108983 A | | 9/2016 | |
| KR | 10-2017-0004401 A | | 1/2017 | |
| KR | 20170004401 A | * | 1/2017 | |
| KR | 20170022290 A | * | 3/2017 | |
| KR | 102099449 B1 | * | 4/2020 | |
| KR | 102226519 B1 | * | 3/2021 | |
| WO | WO-2016061279 A1 | * | 4/2016 | ............ A61B 5/4833 |
| WO | WO-2017218951 A1 | * | 12/2017 | ............ A61C 7/002 |
| WO | WO-2019108978 A1 | * | 6/2019 | ............ A61C 19/045 |
| WO | WO-2019112244 A2 | * | 6/2019 | ............ A61C 7/00 |

\* cited by examiner

APPARATUS CONFIGURED TO BE ATTACHABLE AND DETACHABLE TO AND FROM ORAL CAVITY

FIELD

The present disclosure relates to a device configured to be removably mounted in an oral cavity.

BACKGROUND

An orthodontic appliance for orthodontics or an artificial tooth that can replace a tooth is widely used. The orthodontic appliance or the artificial tooth may be configured to be fixed in an oral cavity, or may be configured to be attached to or detached from the oral cavity by a patient. For example, the orthodontic appliance includes a fixed type orthodontic appliance attached to an oral cavity and detached at the end of treatment, and a removable orthodontic appliance configured to be removably mounted in the oral cavity. The artificial tooth includes an artificial tooth (e.g., dental implant) configured to be fixed in an oral cavity and an artificial tooth (e.g., denture) configured to be attached to or detached from the oral cavity by a patient.

In the case of the removable orthodontic appliance, the appliance can be attached to or detached from the oral cavity according to user's will. Accordingly, the user may not mount the orthodontic appliance for a recommended period of time, and in this case, the treatment effect of the orthodontic appliance becomes poor. Further, the appliance configured to be removably mounted in the oral cavity has a high risk of loss, and if the user lost the appliance, it is necessary to re-create a new appliance for the treatment of the user.

In addition, a user typically visits a hospital to measure biometric information to grasp the user's health condition such as a sleep pattern (e.g., snoring, sleep apnea, etc.) and disease of the user. However, the environment for measuring the biometric information may not be familiar to the patient, these environmental factors may affect the result of the biometric information measurement, and it takes a considerable period of time to obtain the biometric information measurement result.

Various embodiments of the present disclosure may provide a device configured to be removably mounted in an oral cavity to solve the above-mentioned problems or other problems.

SUMMARY

In accordance with an embodiment of the present disclosure, there is provided a device to be removably mounted in at least a portion of an oral cavity, the device including: an antenna; a plurality of markers disposed inside the device and configured to be movable inside the device to measure positions of a first tooth and a second tooth among a plurality of teeth in the oral cavity; a sensor module configured to measure positions of the plurality of markers, and measure at least one of a distance between a reference point set in the device and at least one of the first tooth and the second tooth and a distance between the first tooth and the second tooth based on the measured positions of the plurality of markers; and a communication module configured to transmit to an external device at least one of information about the measured distance between the reference point set in the device and the at least one of the first tooth and the second tooth and information about the measured distance between the first tooth and the second tooth through the antenna.

The communication module may transmit to the external device at least one of the measured distance between the reference point set in the device and the at least one of the first tooth and the second tooth and the measured distance between the first tooth and the second tooth through the antenna through a connected network based on IP (internet protocol) address assigned to the device.

The device may include a GPS (global positioning system) module configured to receive a GPS signal through the antenna, wherein the communication module transmits the received GPS signal to the external device.

The device may further include a processor, wherein, when an information transmission request is received from the external device, the processor controls the communication module to transmit to the external device at least one of the measured distance between the reference point set in the device and the at least one of the first tooth and the second tooth and the measured distance between the first tooth and the second tooth.

The device may further include a processor, wherein the processor measures a movement direction and a movement amount of at least one of the first tooth and the second tooth based on at least one of the measured distance between the reference point set in the device and the at least one of the first tooth and the second tooth and the measured distance between the first tooth and the second tooth, and determine whether or not the device is mounted in the oral cavity based on the measured movement direction and movement amount of the at least one of the first tooth and the second tooth.

The processor may determine that the device is not mounted in the oral cavity when the movement direction of the at least one of the first tooth and the second tooth measured during a preset time is different from a preset movement direction or when the movement amount of the at least one of the first tooth and the second tooth measured during the preset time falls outside a set range.

When it is determined that the device is not mounted in the oral cavity, the processor may control the communication module to transmit to the external device a message requesting mounting of the device or a message of warning for loss of the device.

The device may further include a processor; and a memory storing a plurality of health-related information associated with biometric information, wherein the sensor module measures at least one of respiratory volume, oxygen concentration, electromyogram, and concentration or pH of a volatile sulfur compound gas, and wherein the processor determines whether or not at least one value of the respiratory volume, the oxygen concentration, the electromyogram, and the concentration or pH of the volatile sulfur compound gas is out of a range corresponding to the at least one value included in the biometric information among ranges set for the respiratory volume, the oxygen concentration, the electromyogram, and the concentration or pH of the volatile sulfur compound gas, and, when the at least one value falls outside the corresponding range, controls the communication module to transmit to the external device at least one health-related information associated with at least a portion of the biometric information having the at least one value among the health-related information associated with the biometric information.

The device may further include a processor, wherein the processor controls the communication module to transmit to the external device a message of warning for loss of the device when a strength of a signal received from the external device is less than a preset first value, and controls the communication module to transmit to the external device a message requesting mounting of the device when the strength of the signal received from the external device is greater than or equal to the preset first value and less than a preset second value.

In accordance with another embodiment of the present disclosure, there is provided a device to be removably mounted in at least a portion of an oral cavity, the device including:

an antenna; a plurality of markers disposed inside the device and configured to be movable inside the device to measure positions of a first tooth and a second tooth among a plurality of teeth in the oral cavity; a sensor module configured to measure positions of the plurality of markers, and measure at least one of a distance between a reference point set in the device and at least one of the first tooth and the second tooth and a distance between the first tooth and the second tooth based on the measured positions of the plurality of markers; a communication module configured to communicate with an external device through the antenna; and a processor configured to determine whether or not the device is mounted in the oral cavity based on at least one of the measured distance between the reference point set in the device and the at least one of the first tooth and the second tooth and the measured distance between the first tooth and the second tooth, and control the communication module to transmit to the external device a message requesting mounting of the device or a message of warning for loss of the device when it is determined that the device is not mounted in the oral cavity.

The processor may control the communication module to transmit to the external device a message of warning for loss of the device when a strength of a signal received from the external device is less than a preset first value, and control the communication module to transmit to the external device a message requesting mounting of the device when the strength of the signal received from the external device is greater than or equal to the preset first value and less than a preset second value.

The processor may measure a movement direction and a movement amount of at least one of the first tooth and the second tooth based on at least one of the measured distance between the reference point set in the device and the at least one of the first tooth and the second tooth and the measured distance between the first tooth and the second tooth, and determine whether or not the device is mounted in the oral cavity based on the measured movement direction and the movement amount of the at least one of the first tooth and the second tooth.

The processor may determine that the device is not mounted in the oral cavity when the movement direction of the at least one of the first tooth and the second tooth measured during a preset time is different from a preset movement direction or when the movement amount of the at least one of the first tooth and the second tooth measured during the preset time falls outside a set range.

With the device configured to be removably mounted in the oral cavity according to various embodiments of the present disclosure, it is possible to measure information available for determining whether or not the device is mounted or the location of the device and biometric information of the user through a sensor disposed in the device. By providing the user with information on whether or not the device is mounted or information on the location of the device which is determined based on various measured information and health-related information associated with the measured biometric information, it is possible to prevent the poor effect of the device or reduce the risk for the loss of the device, and provide suitable health-related information to the user.

DETAILED DESCRIPTION OF THE EMBODIMENTS

Figure 1:
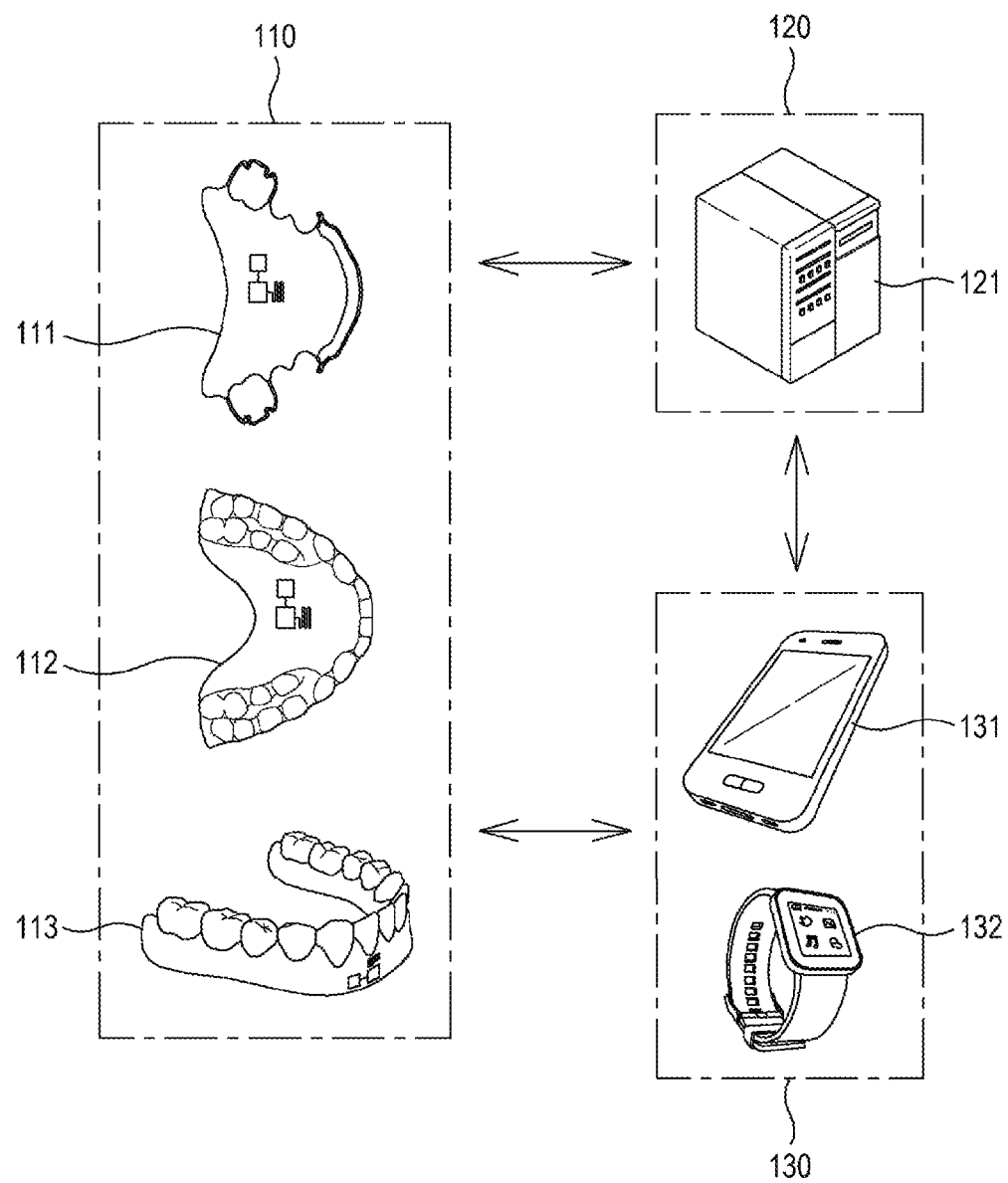
FIG. 1 illustrates a device configured to be removably mounted in an oral cavity according to an embodiment of the present disclosure, and a plurality of external electronic devices communicating with the device.

Embodiments of the present disclosure are exemplified for the purpose of illustrating the technical spirit of the present disclosure. The scope of the claims according to the present disclosure is not limited to the embodiments presented below or the specific description of these embodiments.

All technical terms and scientific terms used in the present disclosure, unless defined otherwise, have a meaning generally understood by a person skilled in the art to which the present disclosure belongs. All terms used in the present disclosure are selected for the purpose of more clearly describing the present disclosure and are not selected to limit the scope of the claims according to the present disclosure.

It should be understood that expressions, such as "comprising", "including" and "having" as used in the present disclosure are open-ended terms which imply the possibility of including other embodiments, unless otherwise stated in the phrase or sentence in which the expression is included.

An expression of the singular described in the present disclosure may encompass the meaning of the plural unless otherwise stated, and the same applies to the expressions of the singular described in the claims.

Expressions such as "first" and "second" used in the present disclosure are used to distinguish a plurality of components from each other, and do not limit the order or importance of the components.

The term "module" used in the present disclosure means software, or hardware components such as a field-programmable gate array (FPGA) and an application specific integrated circuit (ASIC). However, "module" is not limited to hardware and software. The "module" may be configured to be in an addressable storage medium, or may be configured to reproduce one or more processors. Thus, as an example, "module" includes components such as software components, object-oriented software components, class components and task components, and processors, functions, attributes, procedures, subroutines, segments of program codes, drivers, firmware, microcode, circuits, data, databases, data structures, tables, arrays and variables. The functionality provided within the component and "module" may be combined into a smaller number of components and "modules" or further separated into additional components and "modules".

As used in the present disclosure, the expression "based on" is used to describe one or more factors affecting an action or operation of decision or judgment, described in a phrase or sentence containing the expression, but the expression does not exclude additional factors that influence the action or operation of decision or judgment.

In the present disclosure, when a component is described as being "coupled" or "connected" to another component, the component may be coupled or connected to the another component directly or through other component(s).

Hereinafter, embodiments of the present disclosure will be described with reference to the accompanying drawings. In the accompanying drawings, identical or corresponding elements are given the same reference numeral.

In addition, in the following description of the embodiments, redundant descriptions of the same or corresponding elements may be omitted. However, although descriptions of components are omitted, it is not intended that such components are not included in any embodiment.

FIG. 1 illustrates a device configured to be removably mounted in an oral cavity according to an embodiment of the present disclosure, and a plurality of external electronic devices communicating with the device.

In one embodiment, a device configured to be removably mounted in a user's oral cavity (hereinafter, referred to as an 'intraoral device') 110 may be mounted in or detached from the oral cavity by the user. For example, the intraoral device 110 may include various test or treatment devices, such as orthodontic devices 111 and 112, a denture 113, a jaw joint treatment device, a snoring treatment device, a sleep apnea treatment device and the like, which can be removably mounted in the oral cavity. However, this is for illustrative purposes only, and is not limited thereto, and the intraoral device 110 may include any device that is attachable to or detachable from the oral cavity by a user.

The intraoral device 110 may be configured to communicate with external devices 120 and 130 via wireless communication. In one embodiment, the intraoral device 110 may communicate directly with a first external device 120 remotely located through a connected network based on an IP (internet protocol) address assigned to the intraoral device 110. For example, the intraoral device 110 may communicate with the first external device 120 located at a remote location through cellular communication using at least one of LTE, LTE-A (LTE Advance), code division multiple access (CDMA), wideband CDMA (WCDMA), universal mobile telecommunication system (UMTS), wireless broadband (WiBro), or a global system for mobile communication (GSM). In another embodiment, the intraoral device 110 may communicate with a second external device 130 located at a short distance through short-range wireless communication, and the first external device 120 located at a remote location through the second external device 130. For example, the intraoral device 110 may communicate with the second external device 130 located at the short distance through at least one of wireless fidelity (WiFi), light fidelity (LiFi), Bluetooth, Bluetooth low power (BLE), Zigbee, near field communication (NFC), magnetic secure transmission, radio frequency (RF) or body area network (BAN), and may communicate with the first external device 120 located at the remote location through the second external device 130. Further, the intraoral device 110 may communicate with the first external device 120 or the second external device 130 through a narrow-band Internet of Things (NB-IoT).

The first external device 120 performing wireless communication with the intraoral device 110 may include a server 121 that receives and manages information measured by the intraoral device 110, and the second external device 130 may include a smart phone 131 carried by a user, a wearable device such as a smart watch 132, and the like. However, this is for illustrative purposes only, and is not limited thereto, and the first and second external devices 120 and 130 may include all devices that support wireless communication.

In one embodiment, the intraoral device 110 may measure mounting determination information used to determine whether or not the intraoral device 110 is mounted through a sensor module included in the intraoral device 110. In addition, the intraoral device 110 may measure biometric information of a user through the sensor module included in the intraoral device 110. The intraoral device 110 may transmit at least one of the measured mounting determination information and the measured biometric information to at least one of the first external device 120 and the second external device 130.

In one embodiment, the intraoral device 110 may determine whether or not the intraoral device 110 is mounted using the measured mounting determination information, and transmit the determination result to at least one of the first external device 120 and the second external device 130. In addition, the intraoral device 110 may use strengths of signals received from the first external device 120 and the second external device 130 to determine whether or not the intraoral device 110 is mounted.

In one embodiment, the intraoral device 110 may check the location of the intraoral device 110 using a GPS signal or strengths of signals received from the first external device 120 and the second external device 130, and transmit the information on the location of the intraoral device 110 to the first external device 120 and the second external device 130.

In one embodiment, the first external device 120 and the second external device 130 may determine whether or not the intraoral device 110 is mounted by using the mounting determination information received from the intraoral device 110 or the strength of the signal received from the intraoral device 110. In addition, the first external device 120 and the second external device 130 may check the location of the intraoral device 110 using a GPS signal or the strength of a signal received from the intraoral device 110. Accordingly, the first external device 120 and the second external device 130 may provide information indicating whether or not the intraoral device 110 is mounted or the location of the intraoral device 110.

Further, when receiving information on whether or not the intraoral device 110 is mounted and the location of the intraoral device 110 determined by the intraoral device 110 from the intraoral device 110, the first external device 120 and the second external device 130 may provide the received information through an output device such as a display and/or a speaker. A user or a third party (for example, a dentist) can check the information, provided through the first external device 120 and the second external device 130, about whether or not the intraoral device 110 is mounted in the oral cavity and the location of the intraoral device 110. Accordingly, it is possible to prevent or decrease the reduction of the treatment effect of the intraoral device 110 or the risk for the loss of the intraoral device 110 due to no mounting of the intraoral device 110.

In one embodiment, the intraoral device 110 may be a device used to treat snoring or sleep apnea. Here, the snoring may indicate symptoms in which the breathing passages (for example, upper respiratory tract) such as nasal passages, pharynx and larynx are narrowed to generate sound during sleep. In addition, sleep apnea may indicate symptoms in which as the breathing passage becomes narrower during sleep, breathing stops over a period of time or a certain frequency. For example, the symptom and severity of sleep apnea can be checked based on a variety of biological information such as a flow of air through a nose and a mouth (e.g., respiratory volume), chest and ascites breathing exercises, brain waves, eye movements, blood oxygen saturation, an electrocardiogram, electromyography and the like. For example, the treatment of snoring and sleep apnea may be implemented by comprehensively considering an anatomical structure of a patient, a polysomnography test result, and patient's preference for treatment methods. As a therapy method for snoring and sleep apnea, various devices and methods such as surgery, a positive pressure breathing apparatus, an intraoral device, a weight control, and a posture adjustment may be employed.

According to one embodiment, the intraoral device 110 may be manufactured based on a patient's oral condition. The upper respiratory tract may be widened by the patient wearing the intraoral device 110 adjusted to change the muscle tension or the position of the lower jaw. Further, the intraoral device 110 may not only broaden the upper respiratory tract, but also measure the user's biometric information through a sensor module included in the intraoral device 110.

In one embodiment, the intraoral device 110 may transmit the measured biometric information to at least one of the first external device 120 and the second external device 130. For example, the intraoral device 110 may determine whether to provide health-related information to the user through the measured biometric information. The intraoral device 110 may provide health-related information to the user when the biometric information is out of a set range, and inform the user that he/she should be treated at a hospital. For example, the health-related information may include information on a disease associated with at least a part of the measured biometric information, information on items to be noted for health, and the like. A specific method in which the intraoral device 110 provides health-related information to the user using biometric information will be described later.

In one embodiment, the first external device 120 and the second external device 130 may provide health-related information to a user by using the user's biometric information received from the intraoral device 110. The first external device 120 and the second external device 130 may provide health-related information associated with biometric information through an output device such as a display and/or a speaker. In addition, biometric information may be used to treat a user's sleep pattern, disease, etc. Through the intraoral device 110, biometric information is measured in an environment familiar to the user, and based on the biometric information, the user's health state, such as the user's sleep pattern or disease, can be more accurately grasped.

Figure 2:
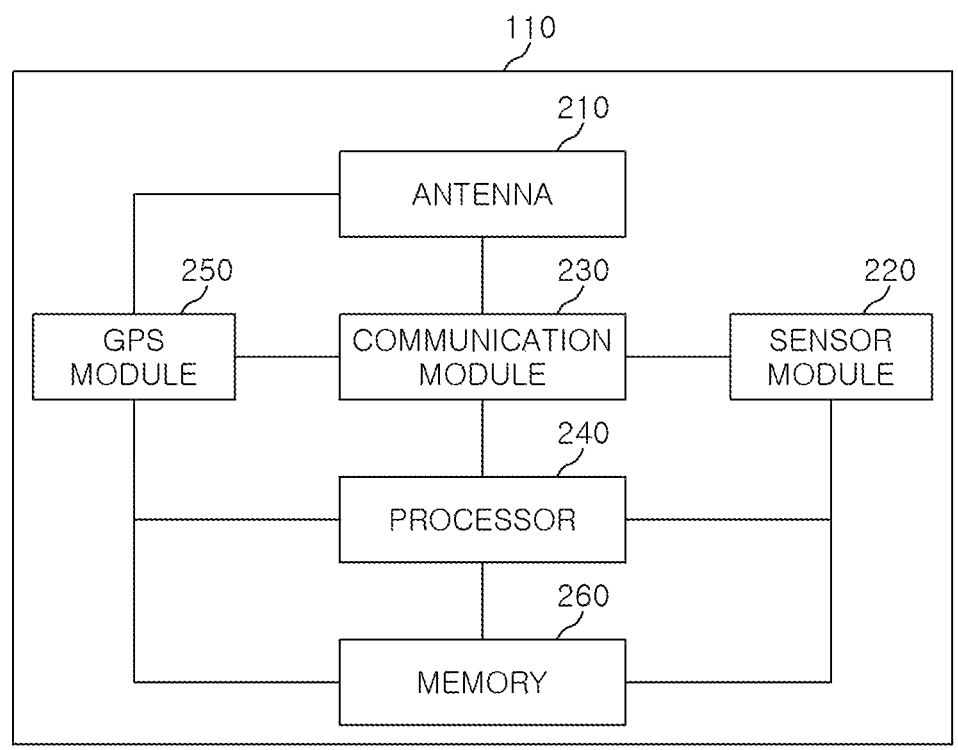
FIG. 2 is a block diagram of the device configured to be removably mounted in an oral cavity.

FIG. 2 is a block diagram of the intraoral device 110 configured to be removably mounted in an oral cavity according to one embodiment of the present disclosure.

In one embodiment, the intraoral device 110 may include an antenna 210, a sensor module 220, a communication module 230, and a processor 240. In addition, the intraoral device 110 may further include a GPS module 250 for receiving a GPS signal and a memory 260 for storing information measured through the sensor module 220 and a plurality of health-related information. The plurality of health-related information may be stored in the memory 260 in association with biometric information measurable through the sensor module 220. The plurality of health-related information may include information on diseases associated with biometric information measurable through the sensor module 220, information on items to be noted for health, and the like. In addition, although not shown, the intraoral device 110 may include a battery for supplying power to each component included in the intraoral device 110.

The antenna 210 may emit or receive a signal in performing wireless communication with an external device (e.g., the first external device 120 and/or the second external device 130 in FIG. 1). For example, the antenna 210 may include a conductive member that can be used to emit or receive a signal. The conductive member may be disposed inside the intraoral device 110 so as not to contact any portion in the user's oral cavity to prevent the user from feeling difference in mounting the intraoral device 110.

The sensor module 220 may measure mounting determination information used to determine whether or not the intraoral device 110 is mounted. For example, the mounting determination information used to determine whether or not the intraoral device 110 is mounted may include information on at least one of temperature, luminance (or illuminance), loudness, acceleration, pressure, and a distance between a reference point set in the intraoral device and at least one tooth in the oral cavity or a distance between a first tooth and a second tooth in the oral cavity. For example, the mounting determination information may include information on at least one value of temperature, luminance (or illuminance), loudness, acceleration, pressure, and a distance between a reference point set in the intraoral device and at least one tooth in the oral cavity or a distance between a first tooth and a second tooth in the oral cavity. However, this is for illustrative purposes only, and is not limited thereto. The sensor module 220 may measure various information available to determine whether or not the intraoral device 110 is mounted or to determine the location of the tooth in the oral cavity, e.g., the distance between the intraoral device 110 and a portion of the oral cavity.

Further, the sensor module 220 may measure biometric information of the user. For example, the biometric information may include information about at least one of respiratory volume, oxygen concentration, electromyogram, and concentration or pH of a volatile sulfur compound gas. Further, the biometric information may include, e.g., information on at least value of respiratory volume, oxygen concentration, electromyogram, and concentration or pH of a volatile sulfur compound gas. However, this is for illustrative purposes only, and the sensor module 220 may measure various biometric information that can be measured in the oral cavity of the user without being limited to the above. For example, the biometric information may also include information on various biological markers for expressing a user's health-related condition, such as saliva's biological buffer, occult blood, and the like.

The sensor module 220 may include various sensors for measuring mounting determination information used to determine whether or not the intraoral device 110 is mounted and biometric information of a user. For example, the sensor module 220 may include a temperature sensor for measuring temperature, a luminance (or illuminance) sensor for measuring luminance (or illuminance), an acoustic sensor for measuring sound, an acceleration for measuring acceleration, a pressure sensor for measuring pressure, a respiratory volume sensor for measuring respiratory volume, an oxygen concentration sensor for measuring oxygen concentration, and/or an electromyography (EMG) sensor for measuring electromyogram. In addition, the sensor module 220 may further include a distance sensor for measuring the distance between the first tooth and the second tooth in the oral cavity. For example, the distance sensor may directly measure the distance between the first tooth and the second tooth in the oral cavity, and may measure the distance between the first tooth and the second tooth through a marker disposed adjacent to the first tooth and the second tooth.

In addition, the sensor module 220 may further include a gas sensor for measuring the concentration of a gas generated in the oral cavity, such as volatile sulfur compound gas. In case that the sensor module 220 includes the gas sensor, the intraoral device 110 may further include an intake port, an air pump, an air filter, and an exhaust port. Furthermore, the sensor module 220 may include an acidity sensor for measuring pH, a buffering capacity sensor for measuring the biological buffering capacity of saliva, an occult blood sensor for measuring occult blood, and the like. In addition, the sensor module 220 may further include a control circuit for controlling at least one sensor included the sensor module 220. Besides, the sensor module 220 may further include various sensors for measuring information according to the type of information.

The communication module 230 may communicate with an external device. For example, the communication module 230 transmits at least one of mounting determination information and biometric information measured by the sensor module 220 to the external device, or receives a signal, e.g., a signal for controlling the intraoral device 110 from the external device.

In one embodiment, the communication module 230 may transmit at least one of the mounting determination information used to determine whether or not the intraoral device 110 is mounted and the user's biometric information measured by the sensor module 220 to the external device through the antenna 210. In one embodiment, the communication module 230 may be connected to a network (e.g., a cellular network) based on the IP address assigned to the intraoral device 110, and may transmit at least one of mounting determination information and biometric information through the connected network to the external device through the antenna 210. In another embodiment, the communication module 230 may transmit through the antenna 210 at least one of mounting determination information and biometric information to an external device connected thereto through short-range wireless communication. According to still another embodiment, the communication module 230 may transmit at least one of mounting determination information and biometric information using an external device connected through short-range wireless communication to another external device remotely located.

In one embodiment, whenever the communication module 230 receives at least one of the mounting determination information and the biometric information from the sensor module 220, the communication module 230 may transmit at least one of the mounting determination information and the biometric information to the external device in real time. According to another embodiment, the communication module 230 may transmit at least one of the mounting determination information and the biometric information to the external device according to a set period. Here, the set period may be adjusted by the processor 240. The processor 240 may be configured to adjust the set period according to a state of a battery included in the intraoral device 110 or to adjust the set period according to a control signal received from an external device.

The communication module 230 may transmit at least one of the mounting determination information and the biometric information to the external device under the control of the processor 240. For example, when receiving a transmission request for at least one of the mounting determination information and the biometric information from the external device, the processor 240 may control the communication module 230 to transmit at least one of the mounting determination information and the biometric information to the external device.

In one embodiment, the processor 240 may determine whether or not the intraoral device 110 is mounted in the oral cavity based on at least one value of temperature, luminance (or illuminance), loudness, acceleration, pressure, and the distance between a reference point set in the intraoral device and at least one tooth in the oral cavity or the distance between a first and a second tooth in the oral cavity, which are included in the mounting determination information measured by the sensor module 220.

For example, the processor 240 may compare at least one value of temperature, luminance (or illuminance), loudness, acceleration, pressure, and the distance between a reference point set in the intraoral device and at least one tooth in the oral cavity or the distance between a first and a second tooth in the oral cavity, which are measured by the sensor module 220, with a threshold value corresponding to the at least one value included in the measured mounting determination information among threshold values set for the temperature, the luminance (or illuminance), the loudness, the acceleration, the pressure, and the distance between the reference point set in the intraoral device and at least one tooth in the oral cavity or the distance between the first and the second tooth in the oral cavity. For each of the mounting determination information measurable by the sensor module 220, a threshold value for determining whether or not the intraoral device 110 is mounted may be preset. For example, when a temperature value is measured by the sensor module 220, the processor 240 may compare the measured temperature value with the threshold value set for the temperature. As another example, when the values of temperature and pressure are measured by the sensor module 220, the processor 240 may compare the measured temperature value with the threshold value set for the temperature, and compare the measured pressure value with the threshold value set for the pressure. Based on the comparison result, it is possible to determine whether or not the intraoral device 110 is mounted in the oral cavity.

As still another example, the processor 240 may measure a distance between a reference point set in the intraoral device 110 and at least one tooth in the oral cavity or a distance between a first tooth and a second tooth in the oral cavity in the sensor module 220. For example, the reference point may be set to any point in the intraoral device 110 that can be measured by the sensor module 220. For example, the reference point may be set to a position of one of the markers included in the intraoral device 110 or may be set to a position of the sensor module 220. In addition, the sensor module 220 may measure the positions of the teeth through markers disposed adjacent to the teeth in the oral cavity, and measure a distance between at least one tooth in the oral cavity and the set reference point or a distance between a first tooth and a second tooth in the oral cavity based on the measured positions. However, this is for illustrative purposes only, and the present disclosure is not limited thereto. The positions of the teeth in the oral cavity may be measured in various ways, and the distance between the reference point and at least one tooth in the oral cavity or the distance between the first tooth and the second tooth in the oral cavity may be measured based on the measured positions.

For example, the processor 240 may measure a movement direction and a movement amount of a tooth to be corrected based on the measured reference point and the distance between at least one tooth in the oral cavity or the distance between a first tooth and a second tooth in the oral cavity. When the movement direction of the tooth to be corrected measured during a preset time is different from a preset movement direction or when the movement amount of the tooth to be corrected measured during the preset time falls outside a set range, the processor 240 may determine that the intraoral device 110 is not mounted in the oral cavity or that there is an abnormality in the position of the moving tooth.

In one embodiment, the processor 240 may adjust a threshold value set for each of the mounting determination information measurable in the sensor module 220. For example, the processor 240 may adjust the threshold value for temperature based on temperature information obtained from an external device. As another example, the processor 240 may adjust the threshold value for luminance (or illuminance) to vary over time. As still another example, the processor 240 may allow the threshold value for the distance between the first tooth and the second tooth in the oral cavity to be adjusted according to the course of orthodontic treatment. Further, the processor 240 may adjust a threshold value set for each of the information measurable by the sensor module 220 according to a control signal received from an external device.

The processor 240 may measure a received signal strength indicator (RSSI) received from an external device. The processor 240 may determine whether or not the intraoral device 110 is mounted based on the distance between the intraoral device 110 and the external device determined through the measured signal strength. A detailed method in which the processor 240 determines whether or not the intraoral device 110 is mounted will be described later.

In one embodiment, when the processor 240 determines that the intraoral device 110 is not mounted in the oral cavity, the processor 240 may control the communication module 220 to transmit to an external device one of a message requesting the mounting of the intraoral device 110 or a message of warning for loss of the intraoral device 110. For example, when transmitting a message of warning for loss of the intraoral device 110 to the external device, the processor 240 may transmit information about the location of the intraoral device 110 to the external device along with the warning message.

In one embodiment, the processor 240 may determine whether or not at least one value of a respiratory volume, an oxygen concentration, an electromyogram, and a concentration or pH of a volatile sulfur compound gas, included in the measured biometric information, is out of a range corresponding to the at least one value included in the biometric information among ranges set for the respiratory volume, the oxygen concentration, the electromyogram, and the concentration or pH of the volatile sulfur compound gas. For each of the biometric information measurable by the sensor module 220, a range that is a reference for determining whether to provide health-related information to a user may be set in advance. For example, when the biometric information is measured, the processor 240 stores the biometric information in the memory 260, and based on the biometric information accumulated in the memory 260, may set a range for each of respiration volume, oxygen concentration, electromyography, and concentration or pH of the volatile sulfur compound gas. Through this, a range for each of the respiratory volume, the oxygen concentration, the electromyography, and the concentration or pH of the volatile sulfur compound gas may be set according to the individual biological characteristics. In addition, the processor 240 may set or adjust the range for each of the respiratory volume, the oxygen concentration, the electromyography, and the concentration or pH of the volatile sulfur compound gas according to control signals for setting or adjusting the ranges received through the first and second external devices 120 and 130.

For example, when the value of the respiratory volume is measured by the sensor module 220, the processor 240 may determine whether the measured respiratory volume is outside the range set for the respiratory volume. As another example, when the oxygen concentration and EMG values are measured by the sensor module 220, the processor 240 may determine whether the measured oxygen concentration and EMG values are outside the respective ranges set for the oxygen concentration and EMG. The processor 240 may control the communication module 230 to transmit information on the determination result to an external device. The determination result may be used to determine whether the first external device 120 and the second external device 130 provide health-related information to the user. In addition, the determination result may be used to grasp the user's health status, such as a user's sleep pattern or disease.

In one embodiment, when the at least one value included in the biometric information is out of the corresponding range, the processor 240 may transmit, among the plurality of health-related information stored in the memory 260, at least one health-related information associated with at least a part of the biometric information having the at least one value out of the range to the second external device 120. The second external device 120 may display the received at least one health-related information.

In one embodiment, the GPS module 250 may receive a GPS signal from a satellite through the antenna 210. The GPS signal can be used to locate the intraoral device 110 in the oral cavity.

The communication module 230 may be configured to transmit the GPS signal received through the GPS module 250 to the external device through the antenna 210. In one embodiment, the communication module 230 may transmit the GPS signal to the external device in real time whenever the GPS signal is received from the GPS module 250. In another embodiment, the communication module 230 may transmit the GPS signal to the external device according to a set period. The set period may be adjusted by the processor 240. The processor 240 may be configured to adjust the set period according to a state of a battery included in the intraoral device 110 or to adjust the set period according to a control signal received from the external device.

In one embodiment, the communication module 230 may transmit the GPS signal to the external device under the control of the processor 240. For example, when a transmission request for the GPS signal is received from the external device, the processor 240 may control the communication module 230 to transmit the GPS signal to the external device.

The processor 240 may check the location of the intraoral device 110 using the GPS module 250 and/or the communication module 230. In one embodiment, the processor 240 may check the location of the intraoral device 110 using the GPS signal received from the GPS module 250. According to another embodiment, the processor 240 may check the location of the intraoral device 110 using the strength of a signal received from the external device through the communication module 230. For example, the processor 240 may receive information about the location of the external device from the external device, and identify the location of the intraoral device 110 using the distance between the intraoral device 110 and the external device determined based on the received information on the location of the external device and the strength of the signal received from the external device. In addition, the processor 240 may control the communication module 230 to transmit information on the identified location of the intraoral device 110 to the external device.

In one embodiment, the processor 240 may determine the distance between the external device and the intraoral device 110 based on the GPS signal received from the GPS module 250. For example, the processor 240 may receive information about the location of the external device from the external device, and determine the distance between the external device and the intraoral device 110 based on the received information on the location of the external device and the GPS signal.

In one embodiment, the processor 240 may transmit to the external device one of a message requesting the mounting of the intraoral device 110 or a message of warning for loss of the intraoral device 110 based on the determined distance between the external device and the intraoral device 110. For example, when the determined distance between the external device and the intraoral device 110 is greater than or equal to a first set value, the intraoral device 110 may control the communication module 230 to transmit to the external device the message of warning for loss of the intraoral device 110. As another example, when the determined distance between the external device and the intraoral device 110 is less than the first set value and greater than or equal to a second set value set smaller than the first set value, the intraoral device 110 may control the communication module 230 to transmit to the external device the message requesting the mounting of the intraoral device 110.

Figure 3:
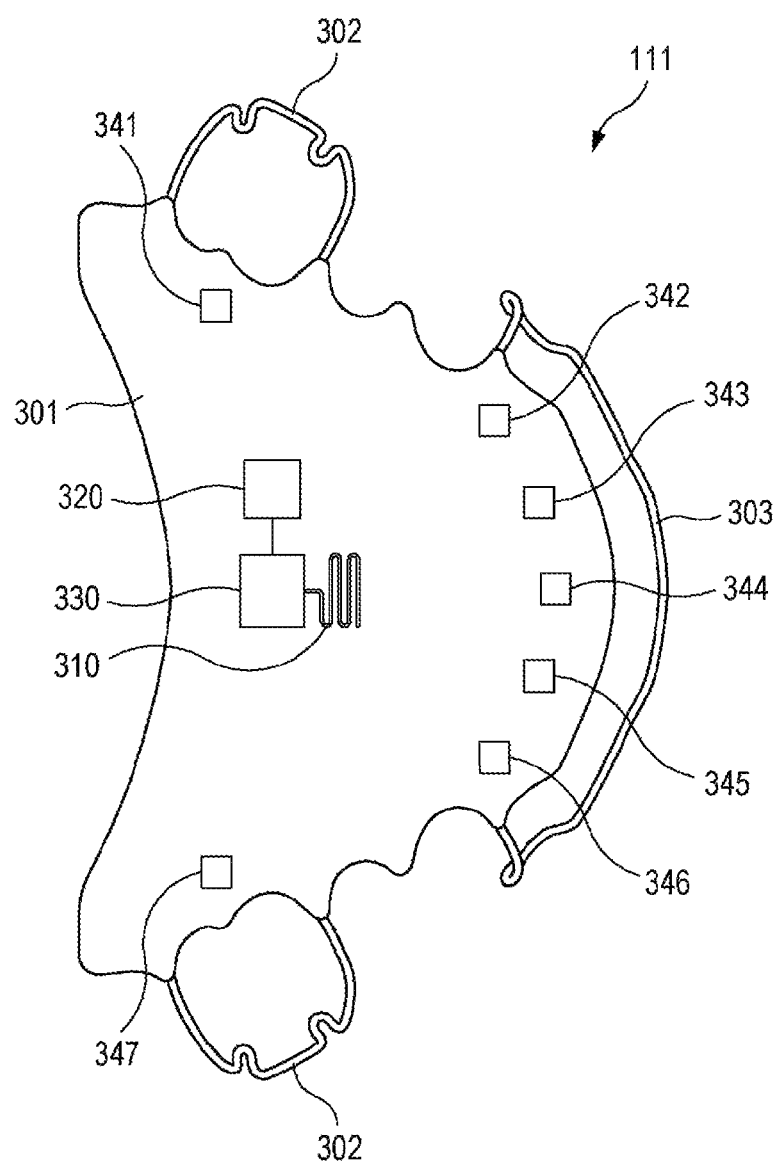
FIG. 3 shows an orthodontic device configured to be removably mounted in an oral cavity according to one embodiment of the present disclosure.
Figure 4:
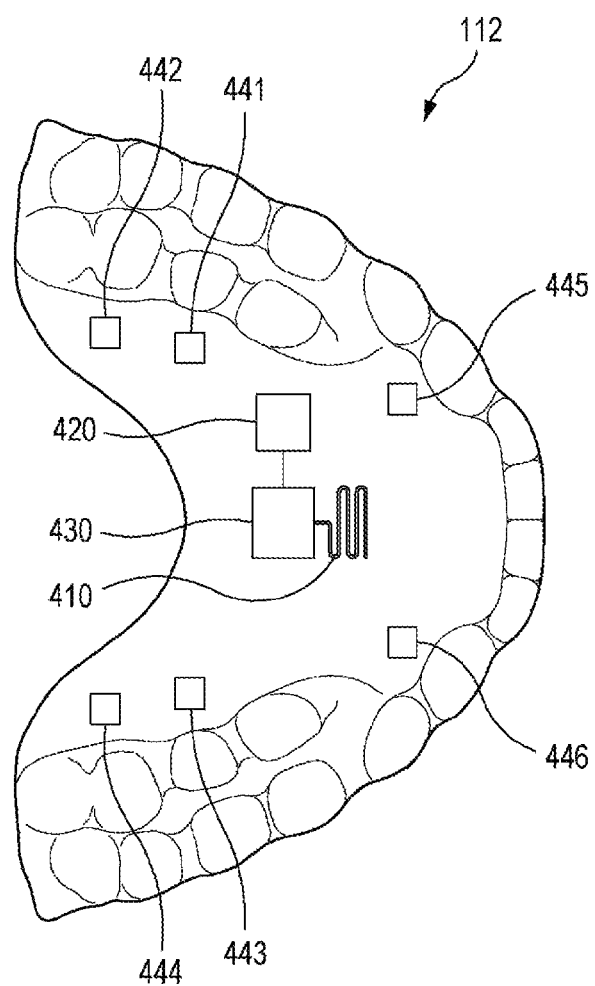
FIG. 4 shows an orthodontic device configured to be removably mounted in an oral cavity according to another embodiment of the present disclosure.

FIGS. 3 and 4 show orthodontic devices configured to be removably mounted in the oral cavity according to embodiments of the present disclosure.

In one embodiment, an orthodontic device 111 configured to be removably mounted in the oral cavity as shown in FIG. 3 may include a base member 301, a holding member 302 and an active member 303. The base member 301 may be formed of a resin, and may be configured to correspond to a shape of at least a portion of the oral cavity, for example, a shape of a palate. The holding member 302 may be supported by at least a portion in the oral cavity such that the orthodontic device 111 is mounted in the oral cavity and the position of the mounted orthodontic device 111 is fixed. For example, various clasps may be used as the holding member 302. The active member 303 may be configured to influence the teeth to be corrected by applying pressure or the like to the teeth to be corrected. For example, a spring, a bow, a retractor, an elastic band, or the like may be used as the active member 303.

In one embodiment, the orthodontic device 111 may include an antenna 310 (e.g., the antenna 210 in FIG. 2), a sensor module 320 (e.g., the sensor module 220 in FIG. 2), and a communication module 330 (e.g., the communication module 230 in FIG. 2). Hereinafter, for convenience of description, there will be described the orthodontic device 111 including the antenna 310, the sensor module 320, and the communication module 330, but the present disclosure is not limited thereto. As described with reference to FIG. 2, the orthodontic device 111 may further include a processor (e.g., the processor 240 in FIG. 2), a GPS module (e.g., the GPS module 250 in FIG. 2), and a battery.

In one embodiment, the antenna 310, the sensor module 320 and the communication module 330 may be disposed inside the base member 301 of the orthodontic device 111. For example, the antenna 310, the sensor module 320, and the communication module 330 may be disposed inside the base member 301 not to directly contact the oral cavity so that a user who mounts the orthodontic device 111 does not feel foreign. As another example, the antenna 310, the sensor module 320, and the communication module 330 may be disposed on one surface of the base member 301 which does not directly contact the oral cavity such that at least a portion thereof is exposed.

In one embodiment, in order to more accurately measure mounting determination information used to determine whether the orthodontic device 111 is mounted and biometric information of a user, the sensor module 320 may be disposed on the base member 301 such that at least portion thereof comes in contact with the oral cavity.

In one embodiment, the orthodontic device 111 may include a plurality of markers 341 to 347. The markers 341 to 347 may be disposed inside the base member 301, and the markers 341 to 347 may be disposed adjacent to at least one of the teeth to be corrected to check the movement of at least one of the teeth to be corrected.

Further, the markers 341 to 347 are configured to be movable inside the base member 301, and at least a portion of the markers 341 to 347 may be exposed to the outside. The markers 341 to 347 may be moved by external force or the like through a moving tube (not shown) serving as a movement path of the markers inside the base member 301. For example, the moving tube may be configured to have a hollow structure such as a tube shape so that the markers 341 to 347 are movable therein.

For example, although not shown, the markers 341 to 347 may be attached to at least one of the teeth to be corrected. Although not shown, the markers 341 to 347 may be directly attached to the teeth to be corrected through the exposed portion or indirectly through a separate connecting member. When the teeth to be corrected move as they are being corrected, the markers 341 to 347 may be moved through the moving tube inside the base member 301 according to the movement direction and the movement amount of the teeth to be corrected. As such, since the markers 341 to 347 are moved through the moving tube according to the movement direction and the movement amount of the teeth to be corrected, the movement direction and the movement amount of the teeth to be corrected can be determined by measuring the positions of the markers 341 to 347.

The sensor module 320 may continuously measure the positions of the markers 341 to 347. Information on the positions of the markers 341 to 347 measured by the sensor module 320 may be used to determine the positions of the teeth, and the determined positions of the teeth may be used to determine whether or not the orthodontic device 111 is mounted or to grasp a tooth movement pattern (e.g., a movement direction, a movement amount, etc.). In addition, for purposes of explanation, there is illustrated in FIG. 3 that the plurality of markers 341 to 347 are included in the orthodontic device 111. However, it is not limited thereto. A single marker can be included in the orthodontic device 111.

In addition, if the plurality of markers 341 to 347 are not included in the orthodontic device 111, the orthodontic device 111 may continuously measure the positions of the teeth in the oral cavity through the sensor module 320. For example, the positions of the teeth in the oral cavity are measured through a proximity sensor included in the sensor module 320, and information about the measured positions of the teeth can be used to determine whether the orthodontic device 111 is mounted.

In one embodiment, an orthodontic device 112 configured to be removably mounted in the oral cavity as shown in FIG. 4 may be configured to surround at least a portion of a teeth group and the palate or mandible.

In one embodiment, the orthodontic device 112 may include an antenna 410 (e.g., the antenna 210 in FIG. 2), a sensor module 420 (e.g., the sensor module 220 in FIG. 2), and a communication module 430 (e.g., the communication module 230 in FIG. 2). Hereinafter, for convenience of description, there will be described the orthodontic device 112 including the antenna 410, the sensor module 420, and the communication module 430, but the present disclosure is not limited thereto. As described with reference to FIG. 2, the orthodontic device 112 may further include a processor (e.g., the processor 240 in FIG. 2), a GPS module (e.g., the GPS module 250 in FIG. 2), and a battery.

In one embodiment, the antenna 410, the sensor module 420 and the communication module 430 may be disposed inside the orthodontic device 112. For example, the antenna 410, the sensor module 420, and the communication module 430 may be disposed inside the orthodontic device 112 not to directly contact the oral cavity so that a user who mounts the orthodontic device 112 does not feel foreign. In addition, the antenna 410, the sensor module 420, and the communication module 430 may be disposed inside a portion of the orthodontic device 112 that surrounds at least a portion of the palate so that it cannot be easily recognized from the outside. As another example, the antenna 410, the sensor module 420, and the communication module 430 may be disposed at the orthodontic device 112 such that at least a portion thereof is exposed.

In one embodiment, in order to more accurately measure mounting determination information used to determine whether the orthodontic device 112 is mounted and biometric information of a user, the sensor module 420 may be disposed on the orthodontic device 112 such that at least a portion thereof comes in contact with the oral cavity.

In one embodiment, the orthodontic device 112 may include a plurality of markers 441 to 446. The markers 441 to 446 may be disposed inside the orthodontic device 112, and the markers 441 to 446 may be disposed adjacent to at least one of the teeth to be corrected to check the movement of at least one of the teeth to be corrected.

Further, the markers 441 to 446 are configured to be movable inside the orthodontic device 112, and at least a portion of the markers 441 to 446 may be exposed to the outside. The markers 441 to 446 may be moved by external force or the like through a moving tube (not shown) serving as a movement path of the markers inside the orthodontic device 112. For example, the moving tube may be configured to have a hollow structure such as a tube shape so that the markers 441 to 446 are movable therein.

For example, although not shown, the markers 441 to 446 may be attached to at least one of the teeth to be corrected. Although not shown, the markers 441 to 446 may be directly attached to the teeth to be corrected through the exposed portion or indirectly through a separate connecting member. When the teeth to be corrected move as they are being corrected, the markers 441 to 446 may be moved through the moving tube inside the orthodontic device 112 according to the movement direction and the movement amount of the teeth to be corrected. As such, since the markers 441 to 446 are moved through the moving tube according to the movement direction and the movement amount of the teeth to be corrected, the movement direction and the movement amount of the teeth to be corrected can be determined by measuring the positions of the markers 441 to 446.

Information on the positions of the markers 441 to 446 measured by the sensor module 420 may be used to determine the positions of the teeth, and the determined positions of the teeth may be used to determine whether or not the orthodontic device 112 is mounted or to grasp a tooth movement pattern. In addition, for purposes of explanation, there is illustrated in FIG. 4 that the plurality of markers 441 to 446 are included in the orthodontic device 112, but it is not limited thereto. A single marker can be included in the orthodontic device 112.

In addition, if the plurality of markers 441 to 446 are not included in the orthodontic device 112, the orthodontic device 112 may continuously measure the positions of the teeth in the oral cavity through the sensor module 420. For example, the positions of the teeth in the oral cavity are measured through a proximity sensor included in the sensor module 420, and information about the measured positions of the teeth can be used to determine whether the orthodontic device 112 is mounted.

Figure 5:
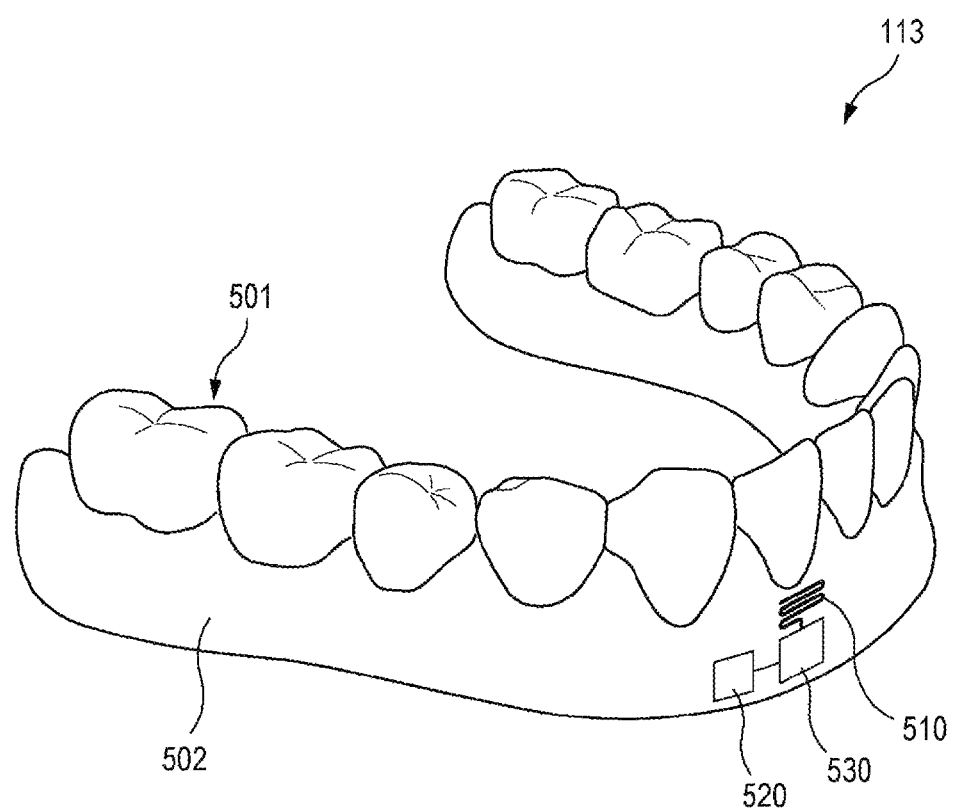
FIG. 5 shows a denture configured to be removably mounted in an oral cavity according to one embodiment of the present disclosure.

FIG. 5 shows a denture configured to be removably mounted in an oral cavity according to one embodiment of the present disclosure.

In one embodiment, a denture 113 configured to be removably mounted in the oral cavity as shown in FIG. 5 may include an artificial tooth portion 501 and a base member 502. The base member 502 may be formed of a resin, and may be configured to correspond to the shape of at least a portion in the oral cavity, for example, the shape of an alveolar bone, to be mounted in the oral cavity. The artificial tooth portion 501 may be configured to be fixed to the base member 502.

In one embodiment, the denture 113 may include an antenna 510 (e.g., the antenna 210 in FIG. 2), a sensor module 520 (e.g., the sensor module 220 in FIG. 2), and a communication module 530 (e.g., the communication module 230 in FIG. 2). Hereinafter, for convenience of description, there will be described the denture 113 including the antenna 510, the sensor module 520, and the communication module 530, but the present disclosure is not limited thereto. As described with reference to FIG. 2, the denture 113 may further include a processor (e.g., the processor 240 in FIG. 2), a GPS module (e.g., the GPS module 250 in FIG. 2), and a battery.

In one embodiment, the antenna 510, the sensor module 520 and the communication module 530 may be disposed inside the base member 502. For example, the antenna 510, the sensor module 520, and the communication module 530 may be disposed inside the denture 113 not to directly contact the oral cavity so that a user who mounts the denture 113 does not feel foreign. As another example, the antenna 510, the sensor module 520, and the communication module 530 may be disposed on one surface of the base member 502 which does not directly contact the oral cavity such that at least a portion thereof is exposed.

In one embodiment, in order to more accurately measure mounting determination information used to determine whether the denture 113 is mounted and biometric information of a user, the sensor module 520 may be disposed on the base member 502 such that at least portion thereof comes in contact with the oral cavity. Further, although not shown, the denture 113 may also include at least one marker when it is necessary to check the position of the artificial tooth portion of the denture 113.

Figure 6:
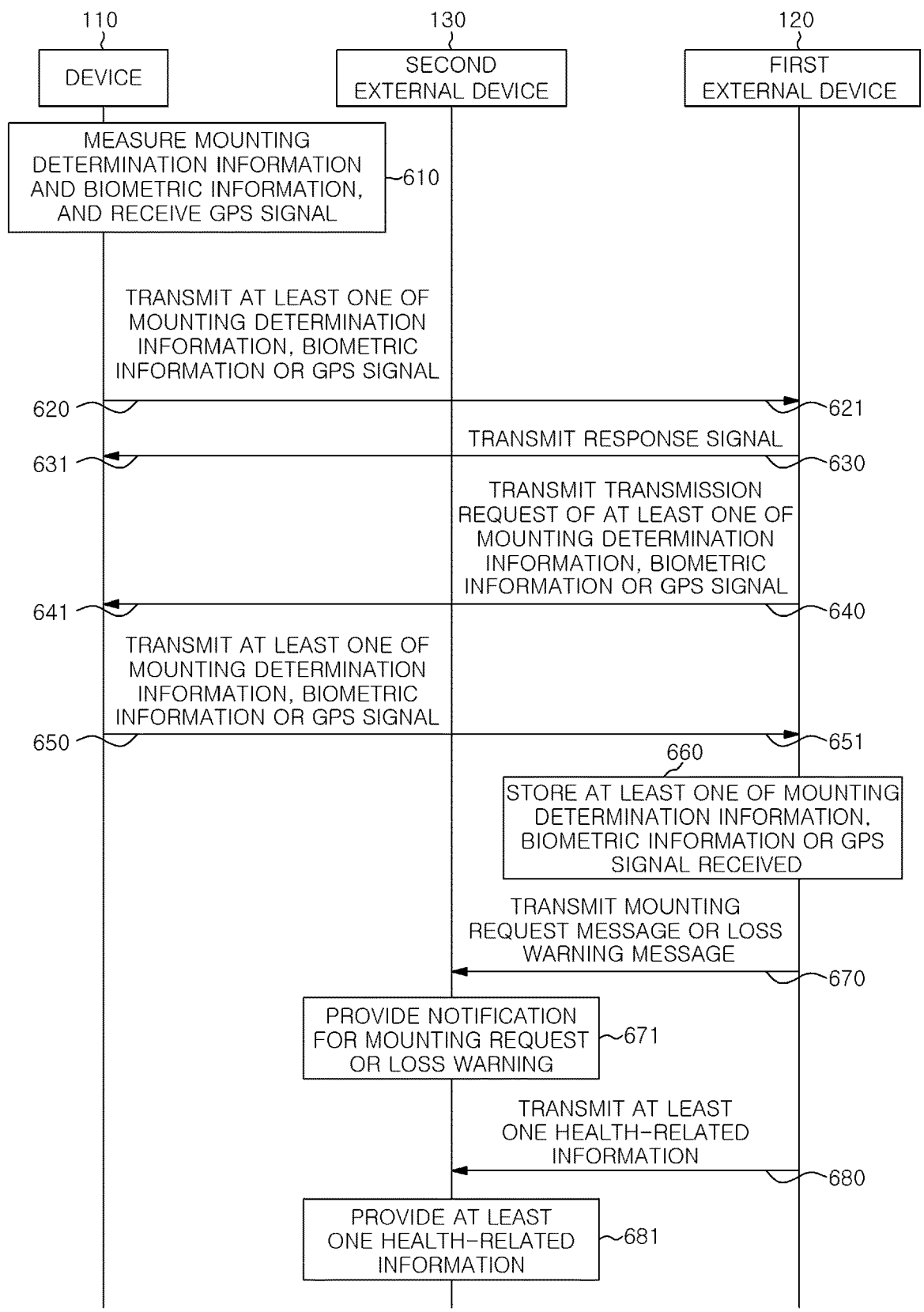
FIG. 6 is a flowchart of a method in which the device configured to be removably mounted in an oral cavity communicates information with the plurality of external electronic devices.

FIG. 6 is a flowchart of a method in which the device configured to be removably mounted in an oral cavity communicates information with a plurality of external electronic devices.

In the flowcharts shown in FIGS. 6 to 10, although process steps, method steps, algorithms and the like have been described in a sequential order, such processes, methods and algorithms may be configured to operate in any suitable order. In other words, the steps of the processes, methods and algorithms described in various embodiments of the present disclosure need not be performed in the order described in the present disclosure. Also, although some steps are described as being performed asynchronously, in other embodiments, some of these steps may be performed simultaneously. Further, the example of a process illustrated in the drawings does not mean that the illustrated process excludes other changes and modifications thereto, and that any of the illustrated process or steps thereof is essential in one or more of various embodiments of the present disclosure, and that the illustrated process is preferred.

In step 610, the intraoral device 110 may measure at least one of mounting determination information used to determine whether or not the intraoral device 110 is mounted and biometric information of a user through the sensor module (e.g., the sensor module 220 in FIG. 2) of the intraoral device 110. For example, the intraoral device 110 may measure the mounting determination information used to determine whether or not the intraoral device 110 is mounted, which includes values of temperature, luminance (or illuminance), loudness, acceleration, pressure, and a distance between a reference point set in the intraoral device and at least one tooth in the oral cavity or a distance between a first tooth and a second tooth in the oral cavity. As another example, the intraoral device 110 may measure the biometric information including values of respiratory volume, oxygen concentration, electromyogram, and concentration or pH of volatile sulfur compound gas. In addition, the intraoral device 110 may receive a GPS signal used to check the location of the intraoral device 110.

In step 620, the intraoral device 110 may transmit at least one of the measured mounting determination information, the measured biometric information, or the GPS signals to at least one of the first external device 120 and the second external device 130. For example, the intraoral device 110 may transmit at least one of the measured mounting determination information, the measured biometric information, or the GPS signals to the second external device 130 through short-range wireless communication. The intraoral device 110 may transmit at least one of the measured mounting determination information, the measured biometric information, or the GPS signals to the second external device 130, and may request the second external device 130 to transmit at least one of the measured mounting determination information, the measured biometric information, or the GPS signals to the first external device 120. The second external device 130 may transmit at least one of the mounting determination information, the biometric information, or the GPS signals to the first external device 120 in response to the request.

As another example, the intraoral device 110 may directly transmit at least one of the measured mounting determination information, the measured biometric information, or the GPS signals to the first external device 120 through a connected network based on an IP address assigned to the intraoral device 110.

In step 630, in response to at least one of the measured mounting determination information, the measured biometric information, or the GPS signal received from the intraoral device 110 or the second external device 130, the first external device 120 may transmit a response indicating the receipt of at least one of the measured mounting determination information, the measured biometric information, or the GPS signal to the intraoral device 110 or the second external device 130. The first external device 120 may transmit the response to the intraoral device 110 directly or through the second external device 130.

In step 640, the first external device 120 may transmit to the intraoral device 110 or the second external device 130 a transmission request of at least one of mounting determination information used to determine whether or not the intraoral device 110 is mounted, biometric information of a user or GPS signals. The first external device 120 may transmit the request to the intraoral device 110 directly or through the second external device 130.

In step 650, in response to the transmission request of at least one of mounting determination information, biometric information, or GPS signals received from the first external device 120, the intraoral device 110 may transmit to the first external device 120 at least one of the measured mounting determination information, the measured biometric information, or the GPS signals. The intraoral device 110 may transmit to the first external device 120 at least one of the measured mounting determination information, the measured biometric information, or the GPS signals directly or through the second external device 130.

In step 660, the first external device 120 may store at least one of mounting determination information, biometric information, or GPS signals received from the intraoral device 110 or the second external device 130. The mounting determination information stored in the first external device 120 may be used to determine whether or not the intraoral device 110 is mounted, and the biometric information may be used to provide health-related information, and the GPS signal may be used to determine the location of the intraoral device 110.

In step 670, the first external device 120 may transmit a message requesting the mounting of the intraoral device 110 to the second external device 130 or a message of warning for loss of the intraoral device 110. The first external device 120 may monitor whether or not the intraoral device 110 is mounted based on at least one of the stored mounting determination information or GPS signals.

For example, when a time period in which it is determined that the intraoral device 110 is not mounted exceeds a preset first time period as a result of monitoring, the first external device 120 may transmit a message requesting the mounting of the intraoral device 110 to the second external device 130.

As another example, when the time period in which it is determined that the intraoral device 110 is not mounted exceeds a preset second time period larger than the first time period as a result of monitoring, the first external device 120 may transmit a message of warning for loss of the intraoral device 110 to the second external device 130.

In addition, even if the time period in which it is determined that the intraoral device 110 is not mounted does not exceed the first time period or the second time period greater than the preset first time period, the first external device 120 may transmit a message of warning for loss of the intraoral device 110 to the second external device 130 based on the location of the second external device 130 and the location of the intraoral device 110. For example, the first external device 120 may receive GPS signals from the intraoral device 110 and the second external device 130, and check the locations of the intraoral device 110 and the second external device 130 based on the GPS signals. Based on the checked locations of the intraoral device 110 and the second external device 130, the first external device 120 may transmit a message of warning for loss of the intraoral device 110 to the second external device 130 when the distance between the intraoral device 110 and the second external device 130 is greater than or equal to a set distance.

In step 671, when receiving a message requesting the mounting of the intraoral device 110 or a message of warning for loss of the intraoral device 110, the second external device 130 may provide a notification for the mounting request of the intraoral device 110 or the warning for loss of the intraoral device 110. For example, the second external device 130 may display a notification for the mounting request of the intraoral device 110 or the warning for loss of the intraoral device 110 through a display. As another example, the second external device 130 may output a voice or vibration for the mounting request of the intraoral device 110 or the warning for loss of the intraoral device 110.

In one embodiment, the first external device 120 may transmit a message requesting the mounting of the intraoral device 110 to the intraoral device 110 or a message of warning for loss of the intraoral device 110. When receiving a message requesting the mounting of the intraoral device 110 or a message of warning for loss of the intraoral device 110, the intraoral device 110 may display a notification for indicating the mounting request or the loss warning, or output vibration or voice for indicating the mounting request or the loss warning. In this case, the intraoral device 110 may further include a display for displaying a notification for indicating the mounting request or the loss warning. In addition, the intraoral device 110 may further include an output module for outputting vibration or voice for indicating the mounting request or the loss warning.

In step 680, the first external device 120 may transmit to the second external device 130 at least one health-related information associated with at least a part of the biometric information based on the biometric information. The first external device 120 may determine whether to provide health-related information to the user using the received biometric information, and transmit, among the stored health-related information, at least one health-related information associated with at least a part of the received biometric information.

For example, when the concentration of the volatile sulfur compound gas contained in the biometric information is out of a set range based on the biometric information, the first external device 120 may transmit health-related information associated with the volatile sulfur compound, i.e., information on sinusitis, periodontal disease, dental caries, reflux esophagitis, gastritis, kidney disease, and diabetes. However, this is for illustrative purposes only, and the present disclosure is not limited thereto. The first external device 120 may transmit various health-related information associated with at least a part of biometric information having a value outside a set range.

In step 681, when receiving at least one health-related information from the first external device 120, the second external device 130 may provide the received at least one health-related information. For example, the second external device 130 may provide at least one health-related information to a user through an output device (e.g., a display).

Figure 7:
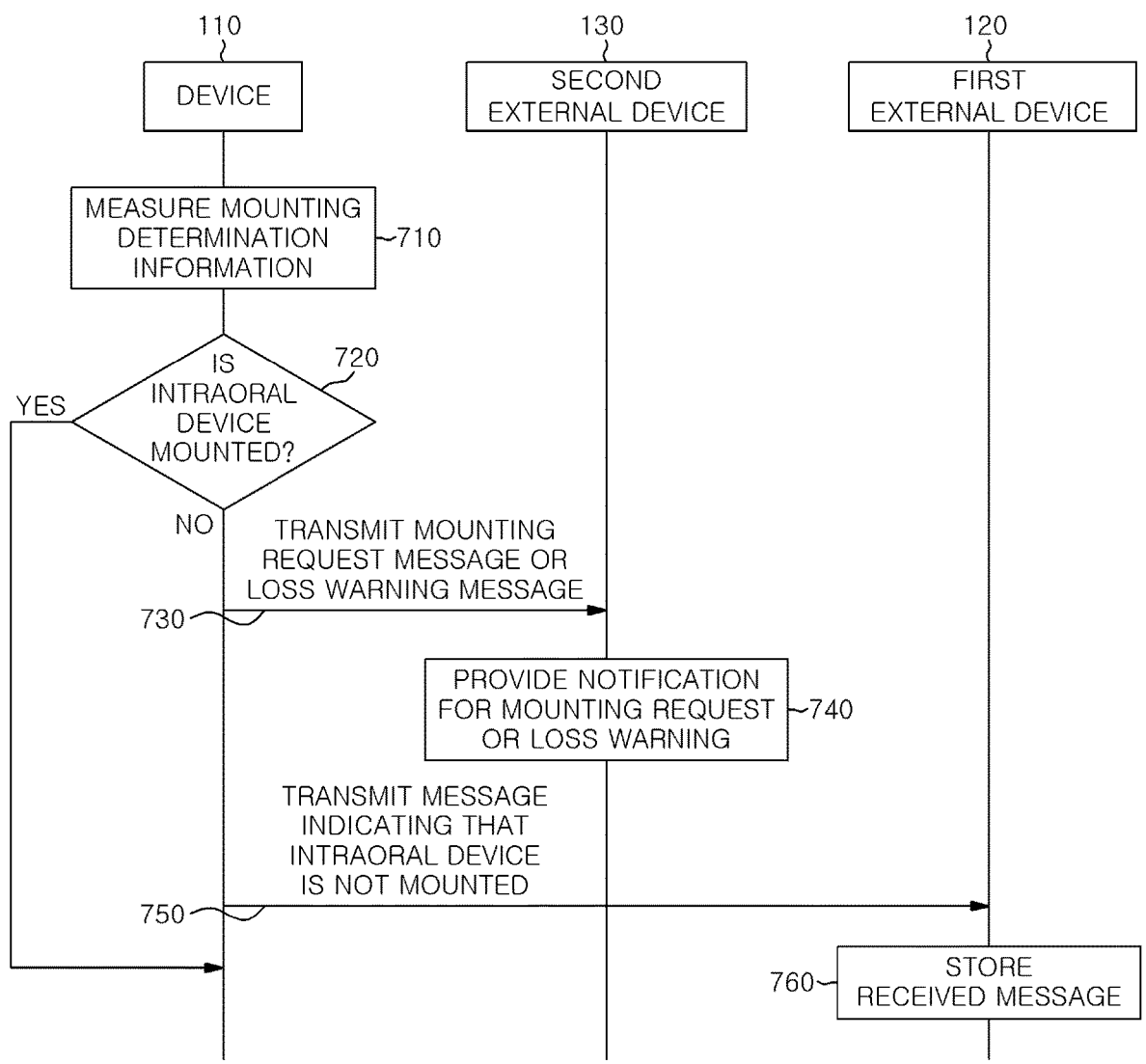
FIG. 7 is a flowchart of a method in which the device configured to be removably mounted in an oral cavity provides information on a mounting state to the plurality of external electronic devices.

FIG. 7 is a flowchart of a method in which a device configured to be removably mounted in an oral cavity provides information on a mounting state to a plurality of external electronic devices.

In step 710, the intraoral device 110 may measure mounting determination information used to determine whether or not the intraoral device 110 is mounted through a sensor module (e.g., the sensor module 220 in FIG. 2) of the intraoral device 110. For example, the intraoral device 110 may measure the mounting determination information which includes values of temperature, luminance (or illuminance), loudness, acceleration, pressure, and a distance between a reference point set in the intraoral device and at least one tooth in the oral cavity or a distance between a first tooth and a second tooth in the oral cavity. In addition, the intraoral device 110 may receive a GPS signal used to check the location of the intraoral device 110.

In step 720, the intraoral device 110 may determine whether or not the intraoral device 110 is mounted based on the measured mounting determination information. Further, the intraoral device 110 may determine whether or not the intraoral device 110 is mounted based on the strength of a signal received from the first external device 120 or the second external device 130. A specific method for determining whether or not the intraoral device 110 is mounted will be described later.

In step 730, if the intraoral device 110 determines that the intraoral device 110 is not mounted in the oral cavity, the intraoral device 110 may transmit one of a message requesting the mounting of the intraoral device 110 or a message of warning for loss of the intraoral device 110 to the second external device 130.

In step 740, when receiving a message requesting the mounting of the intraoral device 110 or a message of warning for loss of the intraoral device 110, the second external device 130 may provide a notification for the mounting request of the intraoral device 110 or the warning for loss of the intraoral device 110. For example, the second external device 130 may display a notification for the mounting request of the intraoral device 110 or the warning for loss of the intraoral device 110 through a display. As another example, the second external device 130 may output a voice or vibration for the mounting request of the intraoral device 110 or the warning for loss of the intraoral device 110.

In step 750, if the intraoral device 110 determines that the intraoral device 110 is not mounted in the oral cavity, the intraoral device 110 may transmit to the first external device 120 a message indicating that the intraoral device 110 is not mounted.

In step 760, when receiving a message indicating that the intraoral device 110 is not mounted, the first external device 120 may store the message indicating that the intraoral device 110 is not mounted. The first external device 120 may manage the mounting history of the intraoral device 110 by storing the message indicating that the intraoral device 110 is not mounted.

Figure 8:
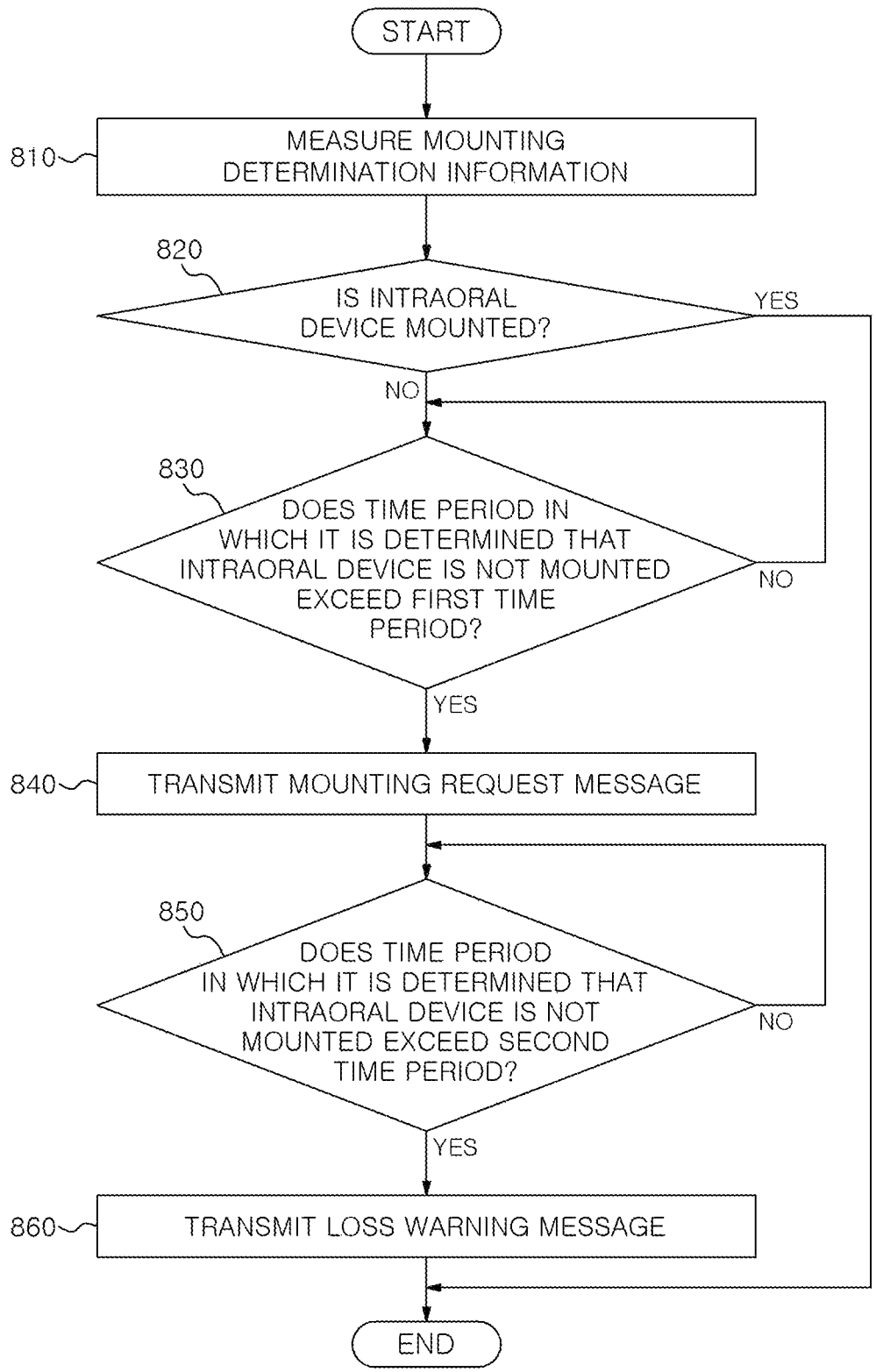
FIG. 8 is a flowchart of a method in which the device configured to be removably mounted in an oral cavity determines whether or not it is mounted using information sensed by a sensor.

FIG. 8 is a flowchart of a method in which a device configured to be removably mounted in an oral cavity determines whether it is mounted using information sensed by a sensor.

In step 810, the intraoral device 110 may measure mounting determination information used to determine whether or not the intraoral device 110 is mounted through a sensor module (e.g., the sensor module 220 in FIG. 2) of the intraoral device 110. For example, the intraoral device 110 may measure temperature, luminance (or illuminance), loudness, acceleration, pressure, and a distance between a reference point set in the intraoral device and at least one tooth in the oral cavity or a distance between a first tooth and a second tooth in the oral cavity.

In step 820, the intraoral device 110 may determine whether or not the intraoral device 110 is mounted based on the measured mounting determination information. The intraoral device 110 may compare values of temperature, luminance (or illuminance), loudness, acceleration, pressure, and the distance between a reference point set in the intraoral device and at least one tooth in the oral cavity or the distance between a first and a second tooth in the oral cavity, which are measured by the sensor module 220, with a threshold value corresponding to at least one measured value among threshold values set for the temperature, the luminance (or illuminance), the loudness, the acceleration, the pressure, and the distance between the reference point set in the intraoral device and at least one tooth in the oral cavity or the distance between the first and the second tooth in the oral cavity. The intraoral device 110 may determine whether or not the intraoral device 110 is mounted based on the comparison result.

For example, when the temperature is measured, the intraoral device 110 may compare the measured temperature value with a threshold value set for the temperature. The intraoral device 110 may determine that the intraoral device 110 is not mounted when the measured temperature value is less than the threshold value set for the temperature.

Further, the threshold value set for the temperature may be adjusted based on temperature information obtained from an external device, and the criterion for determining whether or not the intraoral device 110 is mounted may be changed according to the external environment temperature identified based on the temperature information. For example, the intraoral device 110 may determine that the intraoral device 110 is not mounted when the value of the measured temperature is greater than or equal to the threshold value set for the temperature under the condition that the external environment temperature identified on the basis of the temperature information is higher than a normal body temperature value.

As another example, when the luminance (or illuminance) is measured, the intraoral device 110 may compare a value of the measured luminance (or illuminance) with a threshold value set for the luminance (or illuminance). The intraoral device 110 may determine that the intraoral device 110 is not mounted when the measured luminance (or illuminance) value is out of the threshold value set for the luminance (or illuminance).

As still another example, when the temperature and pressure values are measured, the intraoral device 110 may compare the measured temperature and pressure values with threshold values respectively set for temperature and pressure. The intraoral device 110 may determine that the intraoral device 110 is not mounted when both the measured temperature and pressure values are respectively less than the threshold values set for the temperature and pressure In one embodiment, the intraoral device 110 may determine whether deformation or damage of the intraoral device 110 occurs based on the mounting determination information. For example, when both the measured temperature and pressure values are respectively greater than or equal to the threshold values set for the temperature and pressure, the intraoral device 110 may determine that it is necessary to check for deformation or breakage of the intraoral device 110 and transmit a message therefor to the first and second external devices 120 and 130.

As still another example, when a distance between a first tooth and a second tooth in the oral cavity is measured, the intraoral device 110 may compare the measured distance between the first tooth and the second tooth in the oral cavity with a threshold value set for the distance between the first tooth and the second tooth in the oral cavity. The threshold value set for the distance between the first tooth and the second tooth in the oral cavity may be set as the distance between the first tooth and the second tooth in the oral cavity measured at the time of manufacture or adjustment of the intraoral device 110. The difference between the distance between the first tooth and the second tooth in the oral cavity measured after a predetermined time has elapsed from the time of manufacture or adjustment of the intraoral device 110 and the threshold value is out of a preset range, the intraoral device 110 may determine that the intraoral device 110 is not mounted. Further, the difference between the distance between the first tooth and the second tooth in the oral cavity measured after a predetermined time has elapsed from the time of manufacture or adjustment of the intraoral device 110 and the threshold value is out of the preset range, the intraoral device 110 may determine that an abnormality has occurred in the positions of the teeth.

As described above, the intraoral device 110 may determine whether or not the intraoral device 110 is mounted by comparing the measured mounting determination information with the threshold value set for the measured mounting determination information. Further, in order to more accurately determine whether or not the intraoral device 110 is mounted according to individual characteristics of a user who uses the intraoral device 110 or surrounding environment, the set threshold value may be adjusted according to information or control commands obtained from an external device, and a criterion for determining whether or not the intraoral device 110 is mounted may also be adjusted.

In step 830, the intraoral device 110 may determine whether a time period in which it is determined that the intraoral device 110 is not mounted exceeds a preset first time period. The first time period is a reference time period for determining whether to perform a mounting request for the intraoral device 110, and may be adjusted by the intraoral device 110 or by a control signal received from an external device.

In step 840, the intraoral device 110 may transmit a message requesting the mounting of the intraoral device 110 to the external device when the time period in which it is determined that the intraoral device 110 is not mounted exceeds the preset first time period. Further, the intraoral device 110 may display a notification for requesting the mounting of the intraoral device 110 or output a voice or vibration for requesting the mounting of the intraoral device 110.

In step 850, the intraoral device 110 may determine whether the time period in which it is determined that the intraoral device 110 is not mounted exceeds a preset second time period larger than the first time period. The second time period is a reference time period for determining whether or not to perform a warning for loss of the intraoral device 110, and may be adjusted by the intraoral device 110 or by a control signal received from an external device.

In step 860, when the time period in which it is determined that the intraoral device 110 is not mounted exceeds the preset second time period, the intraoral device 110 may transmit a message of warning for loss of the intraoral device 110 to the external device. Further, the intraoral device 110 may display a notification for the warning for loss of the intraoral device 110 or output a voice or vibration for the warning for loss of the intraoral device 110.

In addition, even if the time period in which it is determined that the intraoral device 110 is not mounted does not exceed the first time period or the second time period, the intraoral device 110 may transmit a message of warning for loss of the intraoral device 110 to the external device 130 based on the location of the intraoral device 110 and the location of the external device connected thereto through short-range wireless communication.

Figure 9:
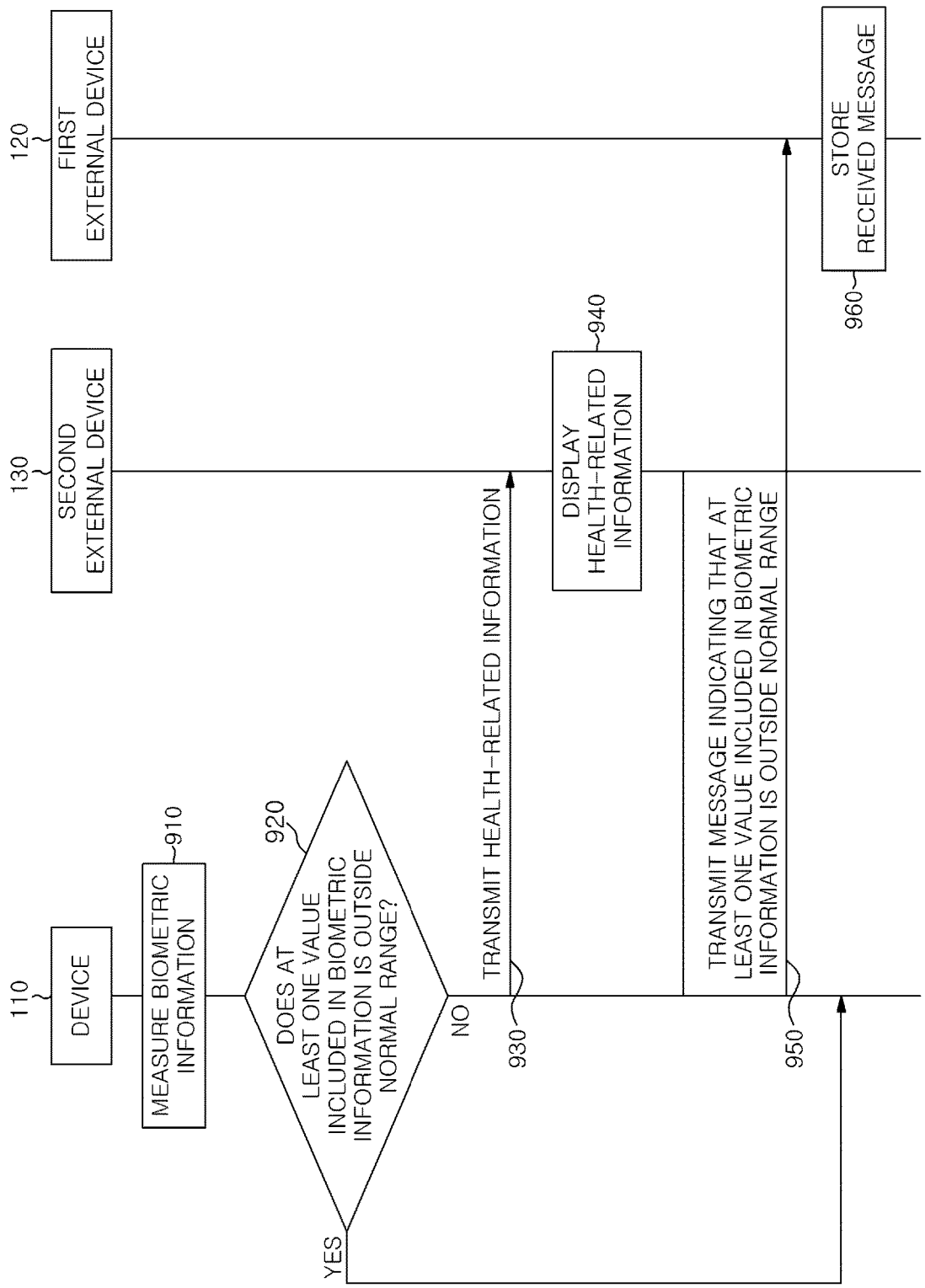
FIG. 9 is a flowchart of a method in which the device configured to be removably mounted in an oral cavity provides health-related information to the plurality of external electronic devices.

FIG. 9 is a flowchart of a method in which a device configured to be removably mounted in an oral cavity provides health-related information to a plurality of external electronic devices.

In step 910, the intraoral device 110 may measure biometric information used to provide health-related information to a user through a sensor module (e.g., the sensor module 220 in FIG. 2) of the intraoral device 110. For example, the intraoral device 110 may measure biometric information including information (e.g., information on measured values) on respiratory volume, oxygen concentration, electromyography, and concentration or pH of a volatile sulfur compound gas.

In step 920, based on the measured biometric information, the intraoral device 110 may determine whether at least one value included in the biometric information is outside a set range. The intraoral device 110 may determine whether at least one value included in the biometric information is out of the set range to determine whether to provide health-related information to the user.

In step 930, when the at least one value of the biometric information is out of the set range, the intraoral device 110 may transmit health-related information associated with at least a part of the biometric information having at least one value included in the biometric information to the second external device 130. The intraoral device 110 may search for health-related information associated with at least a part of the biometric information having at least one value included in the biometric information, among a plurality of health-related information stored in the memory (the memory 260 in FIG. 2) of the intraoral device 110, and transmit the searched health-related information to the second external device 130.

In step 940, when receiving the health-related information, the second external device 130 may provide the received health-related information. For example, the second external device 130 may display health-related information through a display.

In step 950, when the at least one value of the biometric information is out of the set range, the intraoral device 110 may transmit a message indicating that the at least one value of the biometric information is out of the set range to the first external device 120.

In step 960, when receiving a message indicating that at least one value of the biometric information is out of a set range, the first external device 120 may store the received message. The first external device 120 may manage health-related information of the user of the intraoral device 110 by storing a message indicating that at least one value of the biometric information is out of a set range. The user's health-related information managed by the first external device 120 may be used as data for grasping the user's health status when the user visits a hospital later.

Figure 10:
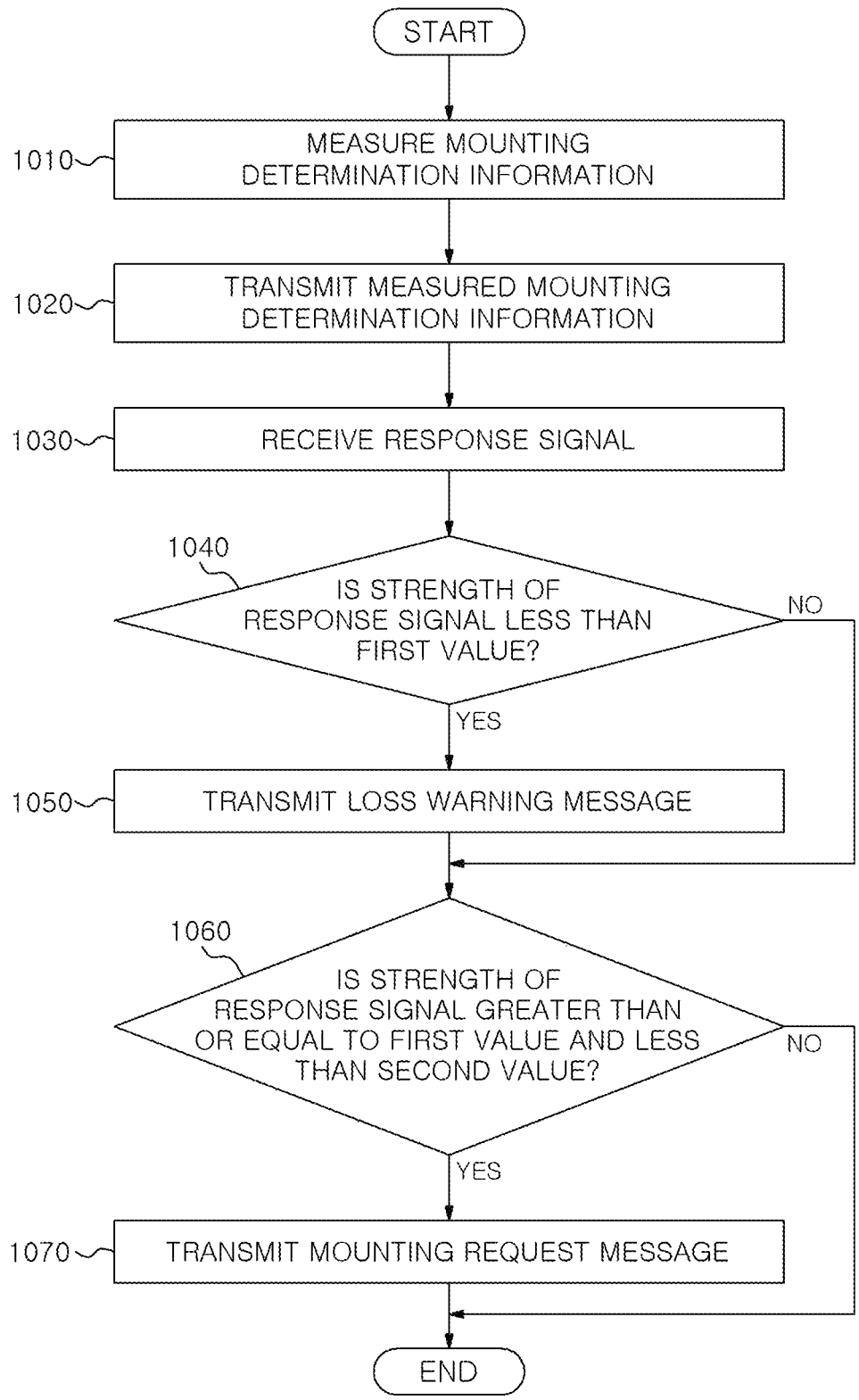
FIG. 10 is a flowchart of a method in which the device configured to be removably mounted in an oral cavity determines whether or not it is mounted using the strength of a received signal.

FIG. 10 is a flowchart of a method in which a device configured to be removably mounted in an oral cavity determines whether it is mounted using the strength of a received signal.

In step 1010, the intraoral device 110 may measure mounting determination information used to determine whether or not the intraoral device 110 is mounted through a sensor module (e.g., the sensor module 220 in FIG. 2) of the intraoral device 110. For example, the intraoral device 110 may measure the mounting determination information such as temperature, luminance (or illuminance), loudness, acceleration, pressure, and a distance between a reference point set in the intraoral device and at least one tooth in the oral cavity or a distance between a first tooth and a second tooth in the oral cavity.

In step 1020, the intraoral device 110 may transmit the measured mounting determination information to an external device. For example, the intraoral device 110 may transmit the mounting determination information measured through a connected network based on an IP address assigned to the intraoral device 110 to the external device. As another example, the intraoral device 110 may transmit the measured mounting determination information to an external device through short-range wireless communication.

In step 1030, the intraoral device 110 may receive a response signal indicating that the measured mounting determination information is received from the external device. When receiving the response signal, the intraoral device 110 may measure the strength of the response signal and determine whether or not the intraoral device 110 is mounted based on the measured signal strength. For example, the intraoral device 110 may determine that the intraoral device 110 is not mounted when the measured signal strength is less than a set value. The set value used to determine whether or not the intraoral device 110 is mounted may be set differently according to an external device that transmits and receives signals.

In step 1040, the intraoral device 110 may determine whether the strength of the signal received from the external device is less than a preset first value. The first value is a reference value for determining whether to perform a warning for loss of the intraoral device 110, and may be adjusted by the intraoral device 110 or by a control signal received from an external device.

In step 1050, when the intensity of the received signal is less than the first value, the intraoral device 110 may transmit a message of warning for loss of the intraoral device 110 to the external device. Further, the intraoral device 110 may display a notification for the warning for loss of the intraoral device 110 or output a voice or vibration for the warning for loss of the intraoral device 110.

In operation 1060, the intraoral device 110 may determine whether the strength of the signal received from the external device is greater than or equal to the first value and less than a second value. The second value is greater than the first value. The second value is a reference value for determining whether to perform a mounting request of the intraoral device 110, and may be adjusted received by the intraoral device 110 or by a control signal from the external device.

In step 1070, when the signal strength received from the external device is greater than or equal to the first value and less than the second value, the intraoral device 110 may transmit a message requesting the mounting of the intraoral device 110 to the external device. In addition, the intraoral device 110 may display a notification for requesting the mounting of the intraoral device 110 or output a voice or vibration to request the mounting of the intraoral device 110.

Figure 11A:
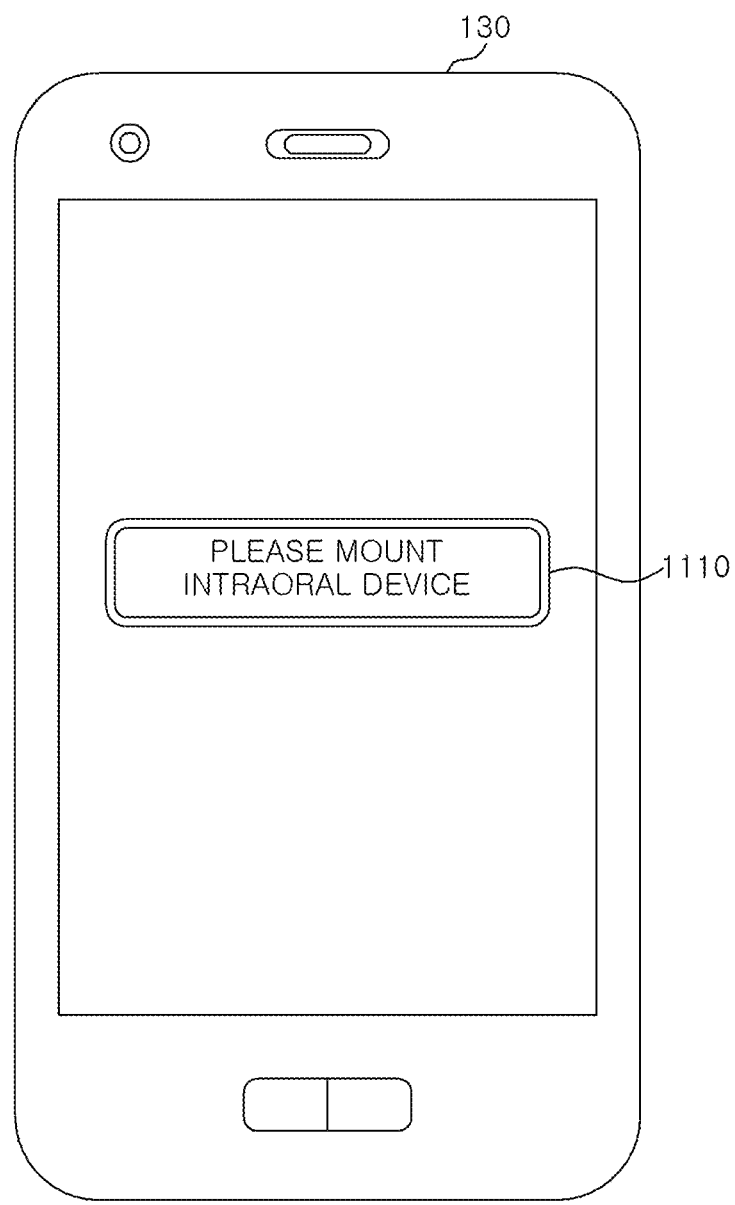
FIGS. 11A and 11B illustrate an external device displaying a notification indicating a mounting request or a risk for loss of the device configured to be removably mounted in an oral cavity.
Figure 11B:
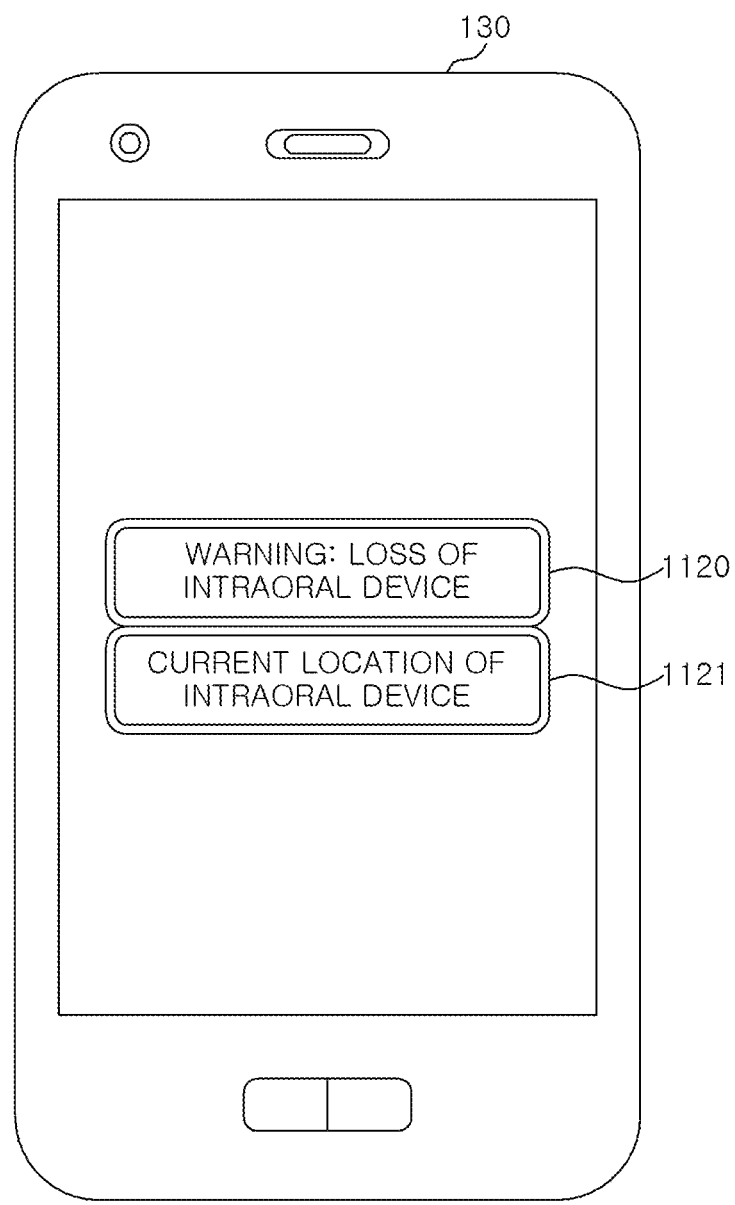

FIGS. 11A and 11B illustrate an external device displaying a notification indicating a mounting request or a risk for loss of the device configured to be removably mounted in an oral cavity.

In one embodiment, the second external device 130 may receive a message requesting the mounting of the intraoral device 110 from the intraoral device 110. As shown in FIG. 11A, when receiving the message, the second external device 130 may display a notification 1110 for requesting to mount the intraoral device 110 through a display. In addition, the second external device 130 may display a notification for requesting the mounting of the intraoral device 110 or output a voice or vibration for requesting the mounting of the intraoral device 110.

In one embodiment, the second external device 130 may receive a message of warning for loss of the intraoral device 110 from the intraoral device 110. As shown in FIG. 11B, when receiving the message, the second external device 130 may display a notification 1120 of warning for loss of the intraoral device 110 through a display. Also, the second external device 130 may further display information 1121 on the location of the intraoral device 110 through the display. The second external device 130 may receive information about the location of the intraoral device 110 from the intraoral device 110, and check information about the location of the intraoral device 110 based on the strength of the GPS signal received from the intraoral device 110 or the signal received from the intraoral device 110. In addition, the second external device 130 may display a notification of warning for loss of the intraoral device 110 or output a voice or vibration of warning for loss of the intraoral device 110.

Figure 12:
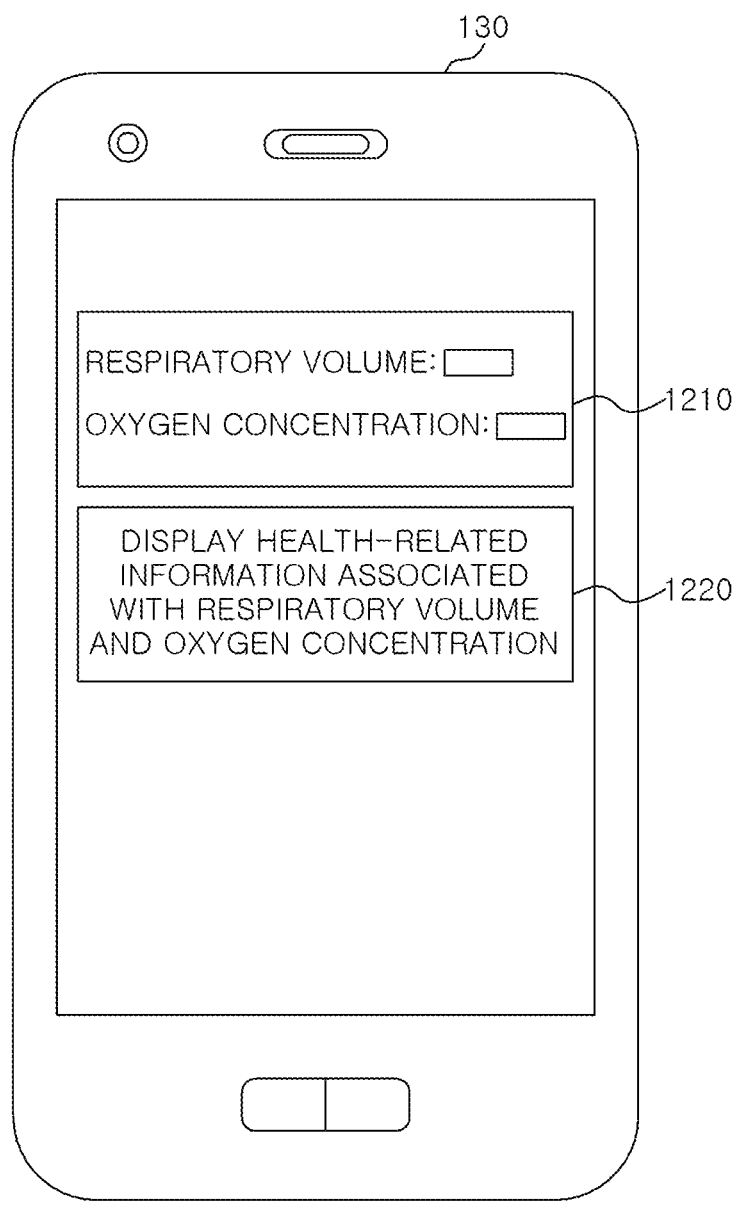
FIG. 12 illustrates an external device displaying health-related information of a user according to one embodiment of the present disclosure.

FIG. 12 illustrates an external device displaying health-related information of a user according to one embodiment of the present disclosure.

In one embodiment, the second external device 130 may receive information about the values of the respiratory volume and oxygen concentration included in the biometric information determined to be outside the set range and health-related information associated with the respiratory volume and oxygen concentration from the first external device 120 or the intraoral device 110. As illustrated in FIG. 12, when receiving information on the values of the respiratory volume and oxygen concentration included in the biometric information and health-related information associated with the respiratory volume and oxygen concentration, the second external device 130 may display the information 1210 on the values of the respiratory volume and oxygen concentration included in the biometric information and the health-related information 1220 thereof through the display. Further, although not shown, the second external device 130 may display a message recommending visiting a hospital for treatment to the user.

Although methods (e.g., operations) according to various embodiments of the present disclosure have been described through specific embodiments, the methods can be embodied as computer readable codes on a computer-readable recording medium. The computer-readable recording medium includes all kinds of recording devices in which data readable by a computer system is stored. The computer-readable recording medium may include ROM, RAM, CD-ROM, magnetic tape, floppy disk, and optical data storage device. In addition, the computer-readable recording medium can be distributed over computer systems connected through a network so that the computer readable codes are stored and executed in a distributed fashion. Further, functional programs, codes, and code segments for implementing the above embodiments can be easily inferred by programmers in the technical field to which the present disclosure pertains.

Although the technical idea of the present disclosure has been described by the examples shown in the accompanying drawings and some embodiments, it should be understood that various substitutions, modifications and changes may be made without departing from the technical spirit and scope of the present disclosure, which can be understood by those skilled in the art to which the present disclosure pertains.

What is claimed is:

1. A device to be removably mounted in at least a portion of an oral cavity, comprising:
   an antenna;
   a plurality of markers disposed inside the device and configured to be movable inside the device to measure positions of a first tooth and a second tooth among a plurality of teeth in the oral cavity;
   a sensor module configured to measure positions of the plurality of markers, and measure at least one of a distance between a reference point set in the device and at least one of the first tooth and the second tooth and a distance between the first tooth and the second tooth based on the measured positions of the plurality of markers; and
   a communication module configured to transmit to an external device at least one of information about the measured distance between the reference point set in the device and the at least one of the first tooth and the second tooth and information about the measured distance between the first tooth and the second tooth through the antenna;
   a processor; and
   a memory storing a plurality of health-related information associated with biometric information, the plurality of health-related information including a predetermined first threshold value set for pressure,
   wherein the sensor module is further configured to measure a temperature value and a pressure value,
   wherein the processor is configured to determine a second threshold value set for temperature based on temperature information obtained from the external device, and compare the measured pressure value and the measured temperature value with the predetermined first threshold value and the determined second threshold value, respectively, and wherein, when the measured temperature value is greater than or equal to the determined second threshold value and the measured pressure value is greater than or equal to the first threshold value, the processor is configured to control the communication module to transmit a message requesting checking for deformation or breakage of the device to the external device.

2. The device to be removably mounted in at least a portion of an oral cavity of claim 1, wherein the communication module transmits to the external device at least one of the measured distance between the reference point set in the device and the at least one of the first tooth and the second tooth and the measured distance between the first tooth and the second tooth through the antenna through a connected network based on an IP (internet protocol) address assigned to the device.

3. The device to be removably mounted in at least a portion of an oral cavity of claim 1, further comprising:
a GPS (global positioning system) module configured to receive a GPS signal through the antenna,
wherein the communication module transmits the received GPS signal to the external device.

4. The device to be removably mounted in at least a portion of an oral cavity of claim 1,
wherein, when an information transmission request is received from the external device, the processor controls the communication module to transmit to the external device at least one of the measured distance between the reference point set in the device and the at least one of the first tooth and the second tooth and the measured distance between the first tooth and the second tooth.

5. The device to be removably mounted in at least a portion of an oral cavity of claim 1,
wherein the processor measures a movement direction and a movement amount of at least one of the first tooth and the second tooth based on at least one of the measured distance between the reference point set in the device and the at least one of the first tooth and the second tooth and the measured distance between the first tooth and the second tooth, and determines whether or not the device is mounted in the oral cavity based on the measured movement direction and movement amount of the at least one of the first tooth and the second tooth.

6. The device to be removably mounted in at least a portion of an oral cavity of claim 5, wherein the processor determines that the device is not mounted in the oral cavity when the movement direction of the at least one of the first tooth and the second tooth measured during a preset time is different from a preset movement direction or when the movement amount of the at least one of the first tooth and the second tooth measured during the preset time falls outside a set range.

7. The device to be removably mounted in at least a portion of an oral cavity of claim 6, wherein, when it is determined that the device is not mounted in the oral cavity, the processor controls the communication module to transmit to the external device a message requesting mounting of the device or a message of warning for loss of the device.

8. The device to be removably mounted in at least a portion of an oral cavity of claim 1,
wherein the sensor module measures the biometric information including at least one of respiratory volume, oxygen concentration, electromyogram, and concentration or pH of a volatile sulfur compound gas, and
wherein the processor determines whether or not at least one value of the respiratory volume, the oxygen concentration, the electromyogram, and the concentration or pH of the volatile sulfur compound gas is out of a range corresponding to the at least one value included in the biometric information among ranges set for the respiratory volume, the oxygen concentration, the electromyogram, and the concentration or pH of the volatile sulfur compound gas, and, when the at least one value falls outside the corresponding range, controls the communication module to transmit to the external device at least one health-related information associated with at least a portion of the biometric information having the at least one value among the health-related information associated with the biometric information.

9. The device to be removably mounted in at least a portion of an oral cavity of claim 1,
wherein the processor controls the communication module to transmit to the external device a message of warning for loss of the device when a strength of a signal received from the external device is less than a preset first value, and controls the communication module to transmit to the external device a message requesting mounting of the device when the strength of the signal received from the external device is greater than or equal to the preset first value and less than a preset second value, the preset second value being greater than the preset first value.

* * * * *